United States Patent
Ghose et al.

(10) Patent No.: US 11,948,677 B2
(45) Date of Patent: Apr. 2, 2024

(54) HYBRID UNSUPERVISED AND SUPERVISED IMAGE SEGMENTATION MODEL

(71) Applicant: GE Precision Healthcare LLC, Milwaukee, WI (US)

(72) Inventors: Soumya Ghose, Niskayuna, NY (US); Jhimli Mitra, Niskayuna, NY (US); Peter M Edic, Albany, NY (US); Prem Venugopal, Clifton Park, NY (US); Jed Douglas Pack, Glenville, NY (US)

(73) Assignee: GE PRECISION HEALTHCARE LLC, Waukesha, WI (US)

(*) Notice: Subject to any disclaimer, the term of this patent is extended or adjusted under 35 U.S.C. 154(b) by 380 days.

(21) Appl. No.: 17/342,280

(22) Filed: Jun. 8, 2021

(65) Prior Publication Data

US 2022/0392616 A1  Dec. 8, 2022

(51) Int. Cl.
| | |
|---|---|
| *G06T 7/00* | (2017.01) |
| *G06N 3/045* | (2023.01) |
| *G06N 3/088* | (2023.01) |
| *G06T 7/10* | (2017.01) |
| *G16H 30/40* | (2018.01) |

(52) U.S. Cl.
CPC ............ *G16H 30/40* (2018.01); *G06N 3/045* (2023.01); *G06N 3/088* (2013.01); *G06T 7/10* (2017.01); *G06T 2207/10081* (2013.01); *G06T 2207/20081* (2013.01); *G06T 2207/20084* (2013.01); *G06T 2207/30101* (2013.01)

(58) Field of Classification Search
CPC ........ G16H 30/40; G16H 50/50; G06N 3/045; G06N 3/088; G06N 3/0455; G06N 7/01; G06N 20/00; G06T 7/10; G06T 2207/10081; G06T 2207/20081; G06T 2207/20084; G06T 2207/30101; G06T 7/11; G06V 2201/03; G06V 10/26; G06V 10/774; G06V 10/82
See application file for complete search history.

(56) References Cited

U.S. PATENT DOCUMENTS

| | | | |
|---|---|---|---|
| 10,441,361 B2 | 10/2019 | Taylor | |
| 11,253,324 B1* | 2/2022 | Bu | ........................ G06T 7/143 |
| 2009/0010540 A1* | 1/2009 | Mullick | ................... G06T 7/38 382/170 |

(Continued)

OTHER PUBLICATIONS

HeartFlow | Webpage https://www.heartflow.com/, last accessed May 24, 2021, 8 pages.

(Continued)

*Primary Examiner* — Van D Huynh
(74) *Attorney, Agent, or Firm* — Amin, Turocy & Watson, LLP

(57) ABSTRACT

Systems and techniques that facilitate hybrid unsupervised and supervised image segmentation are provided. In various embodiments, a system can access a computed tomography (CT) image depicting an anatomical structure. In various aspects, the system can generate, via an unsupervised modeling technique, at least one class probability mask of the anatomical structure based on the CT image. In various instances, the system can generate, via a deep-learning model, an image segmentation based on the CT image and based on the at least one class probability mask.

20 Claims, 12 Drawing Sheets

(56) References Cited

U.S. PATENT DOCUMENTS

| | | | |
|---|---|---|---|
| 2014/0314294 A1* | 10/2014 | Shinagawa | G06T 7/143 |
| | | | 382/131 |
| 2019/0216409 A1* | 7/2019 | Zhou | A61B 6/032 |
| 2021/0093281 A1* | 4/2021 | Madabhushi | G16H 50/20 |
| 2021/0397966 A1* | 12/2021 | Sun | G06T 7/10 |
| 2022/0284584 A1* | 9/2022 | Lee | G06V 10/82 |

OTHER PUBLICATIONS

American Heart Association | Webpage https://www.heart.org/-/media/files/about-US/statistics/2020-heart-disease-and-stroke-ucm_505473.pdf?la=en#:~:text=Cardiovascular%20disease%20(CVD)%2C%20listed,in%20the%20US%20in%202017.&text=Cardiovascular%20diseases%20claim%20more%20lives,Chronic%20Lower%20Respiratory%20Disease%20combined, archived version last accessed on May 25, 2021, 5 pages.

Dempster A. P., et al. | "Maximum Likelihood from Incomplete Data via the EM Algorithm". Journal of the Royal Statistical Society, Series B. 39 (1): 1-38, 1997, 39 pages.

\* cited by examiner

US 11,948,677 B2

HYBRID UNSUPERVISED AND SUPERVISED IMAGE SEGMENTATION MODEL

TECHNICAL FIELD

The subject disclosure relates generally to image segmentation, and more specifically to a hybrid un-supervised and supervised image segmentation model.

BACKGROUND

Measurement and/or estimation of hemodynamics in vascular structures is useful for assessing cardiovascular disease. In existing clinical practice, hemodynamics within a vascular structure can be physically measured via a catheter that is fitted with appropriate transducers. Unfortunately, such physical measurement is highly invasive, time-consuming, expensive, and localized. To address such issues, existing clinical practice has begun to incorporate non-invasive estimation of hemodynamics based on computed tomography (CT) scans that depict vascular structures of interest. Properly estimating the hemodynamics of a vascular structure that is depicted in a CT scan depends upon the CT scan being accurately segmented. Existing deep-learning models can facilitate segmentation of CT scans. However, such existing deep-learning models require huge volumes of training data and often fail to properly generalize.

Accordingly, systems and/or techniques that can address one or more of these technical problems can be desirable.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate hybrid unsupervised and supervised image segmentation are described.

According to one or more embodiments, a system is provided. The system can comprise a computer-readable memory that can store computer-executable components. The system can further comprise a processor that can be operably coupled to the computer-readable memory and that can execute the computer-executable components stored in the computer-readable memory. In various embodiments, the computer-executable components can comprise a receiver component. In various aspects, the receiver component can access a computed tomography (CT) image depicting an anatomical structure. In various instances, the computer-executable components can further comprise a probability component. In various cases, the probability component can generate, via an unsupervised modeling technique, at least one class probability mask of the anatomical structure based on the CT image. In various aspects, the computer-executable components can further comprise an execution component. In various instances, the execution component can generate, via a deep-learning model, an image segmentation based on the CT image and based on the at least one class probability mask.

According to one or more embodiments, the above-described system can be implemented as a computer-implemented method and/or a computer program product.

DETAILED DESCRIPTION

Figure 1:
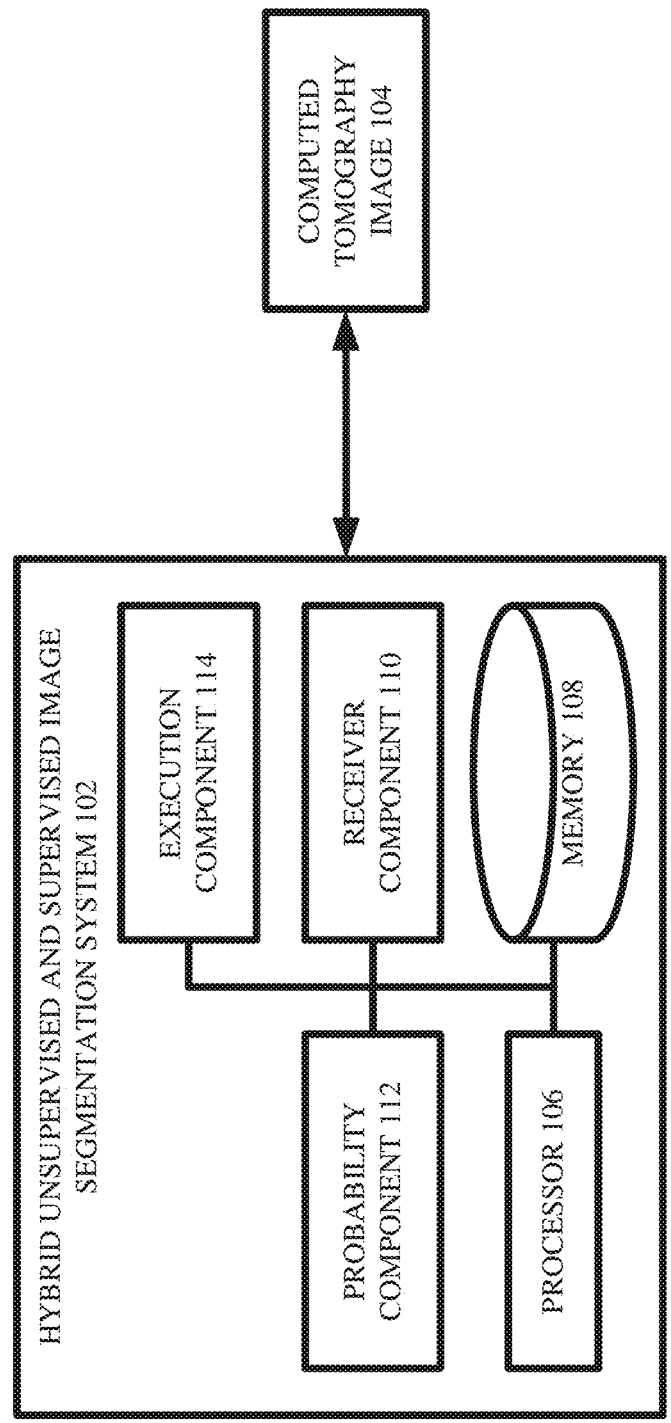
FIG. 1 illustrates a block diagram of an example, non-limiting system that facilitates hybrid unsupervised and supervised image segmentation in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Cardiovascular disease claims more lives each year than all forms of cancer and chronic lower respiratory diseases combined. Indeed, cardiovascular disease accounted for over 859,000 deaths in the United States and 17.8 million deaths worldwide in 2017 alone. Accordingly, techniques for identifying, diagnosing, and/or otherwise assessing cardiovascular disease can be desirable.

Cardiovascular disease in a patient can be assessed by measuring and/or estimating the hemodynamics (e.g., blood pressure, blood flow, fractional flow reserve (FFR)) occurring within the patient's vascular structures (e.g., blood vessels, arteries, lumina).

In existing clinical practice, hemodynamics within a vascular structure can be physically measured via a catheter that is fitted with transducers (e.g., pressure and/or flow transducers). Unfortunately, such physical measurement is highly invasive, time-consuming, and expensive. Moreover, such physical measurement is highly localized. That is, the measured hemodynamics apply only to the vascular structure in which the catheter is inserted and do not necessarily apply to adjoining vascular structures. Accordingly, to physically measure the hemodynamics in such adjoining vascular structures, catheters would have to be inserted into all of such adjoining vascular structures, which is even more invasive, time-consuming, expensive, and/or risky to the patient.

To address such issues, existing clinical practice has begun to incorporate non-invasive estimation of hemodynamics based on computed tomography (CT) images that depict vascular structures of interest. Specifically, a CT image of a vascular structure can be generated by medical imaging equipment (e.g., a CT imaging system), and the CT image can be enhanced and/or analyzed via machine learning models (and/or analytic models) that are configured to estimate, infer, and/or otherwise predict the hemodynamics within the depicted vascular structure. However, proper estimation, inference, and/or prediction of the hemodynamics of the vascular structure that is depicted in the CT image depends upon the CT image being accurately segmented. In other words, if the machine learning models are not able to accurately segment the CT image, and/or if an accurate segmentation of the CT image is not otherwise available to the machine learning models (and/or analytic models), the machine learning models (and/or analytic models) cannot accurately estimate the hemodynamics of the vascular structure depicted in the CT image.

Image segmentation of CT images can be performed by deep-learning models (e.g., artificial neural networks). Specifically, a CT image can, in various cases, be considered as a matrix of pixel-wise Hounsfield unit (HU) values, and a deep-learning model can be trained (e.g., via backpropagation) to receive the CT image as input and to produce an image segmentation of the CT image as output. The image segmentation can be a pixel-wise mask of the CT image that indicates to which of two or more classes each pixel of the CT image belongs. In various cases, the deep-learning model can be considered as a supervised segmentation model. That is, the deep-learning model can be trained in a supervised fashion on training data to perform image segmentation (e.g., the deep-learning model can be fed manually annotated CT images, and the parameters of the deep-learning model can be iteratively updated via backpropagation).

Unfortunately, existing deep-learning models require huge volumes of training data to achieve acceptable segmentation accuracy. Such huge volumes of training data can be highly expensive and time-consuming to procure, and/or can be even more time-consuming to annotate (e.g., indeed, existing clinical practice mainly utilizes manual annotation, which is very time intensive). Moreover, even with such voluminous training data, existing deep-learning models often fail to properly generalize to multi-site settings. For instance, different medical sites (e.g., different hospitals, different hospital departments) can utilize different types and/or amounts of contrast agents, different clinical protocols, different imaging equipment, and/or different reconstruction approaches to create CT images. Such differences can cause different CT images generated by those different medical sites to exhibit different HU intensities, which can adversely affect performance of existing deep-learning models. In other words, an existing deep-learning model that has been extensively trained on CT images provided by one medical site often can exhibit significantly degraded accuracy when segmenting CT images provided by a different medical site. Because of such shortcomings, existing clinical practice usually involves extensive manual editing and/or refinement of image segmentations provided by such existing deep-learning models. Such manual post-processing can consume even more time and resources (e.g., about four to five hours to manually edit/refine CT images). Thus, systems and/or techniques that can address one or more of these technical problems can be desirable.

Various embodiments of the subject innovation can address one or more these technical problems. One or more embodiments described herein include systems, computer-implemented methods, apparatus, and/or computer program products that can facilitate hybrid unsupervised and supervised image segmentation. In various aspects, the inventors of the subject innovation recognized that existing deep-learning models that are trained to perform image segmentation on CT images are structured as single-channel models. That is, such existing deep-learning models are configured to receive as input only the CT image that is desired to be segmented. The inventors realized that such single-channel models are not constrained by any a priori knowledge about the tissue types and/or the context of the anatomical structure depicted in the CT image. Accordingly, the inventors devised various embodiments of the subject innovation to generate such a priori knowledge via unsupervised modeling techniques and to provide such a priori knowledge as additional input to a multi-channel deep-learning model that is configured to produce image segmentations.

Implementation of such a multi-channel deep-learning model as described herein can cause various embodiments of the subject innovation to generate more accurate image segmentations as compared to existing single-channel deep-learning models. Furthermore, implementation of a multi-channel deep-learning model as described herein can cause various embodiments of the subject innovation to require significantly less training data to achieve acceptable segmentation accuracy as compared to existing single-channel deep-learning models.

In various instances, embodiments of the subject innovation can be considered as a computerized tool (e.g., a combination of computer-executable hardware and/or computer-executable software) that can electronically receive a CT image that is desired to be segmented. In various aspects, as described herein, the computerized tool can electronically apply an unsupervised modeling technique to the CT image, thereby yielding one or more class probability masks. In various cases, the computerized tool can electronically feed both the CT image and the one or more class probability masks as input to a deep-learning model, where the deep-learning model is configured to produce an image segmentation based on the CT image and based on the one or more class probability masks. In various instances, if the CT image is an annotated training image, the computerized tool can electronically update, via backpropagation, internal parameters (e.g., weights, biases) of the deep-learning model based on a ground truth annotation associated with the CT image. That is, the deep-learning model can be trained in a supervised fashion. Because the deep-learning model can be trained in a supervised fashion, and because the deep-learning model can be configured to receive as input both the CT image and the one or more class probability masks that are generated by the unsupervised modeling technique, the deep-learning model can be considered as a hybrid unsupervised and supervised multi-channel segmentation model. This is in stark contrast to a purely supervised single-channel segmentation model, which would be configured to receive as input only the CT image and not the one or more class probability masks. Although a CT image is described above and in the description that follows, it should be appreciated that the herein teachings can be applied to a collection of CT images constituting an imaging volume.

As described herein, a hybrid unsupervised and supervised multi-channel segmentation model can exhibit improved segmentation performance (e.g., improved accuracy, reduced training time) as opposed to a purely supervised single-channel segmentation model. Such improved performance can be due to the one or more class probability masks generated by the computerized tool. Indeed, in various cases, the one or more class probability masks that are generated by the computerized tool via the unsupervised modeling technique can be considered as revealing additional patterns, trends, distributions, and/or relations that are hidden within the HU values of the CT image. In other words, such additional patterns, trends, distributions, and/or relations cannot be easily discernable by viewing the CT image alone. So, a purely supervised single-channel segmentation model that is configured to receive as input only the CT image and not the one or more class probability masks can have no access to such additional patterns, trends, distributions, and/or relations. On the other hand, a hybrid unsupervised and supervised multi-channel segmentation model that is configured to receive as input both the CT image and the one or more class probability masks can have access to such additional patterns, trends, distributions, and/or relations, which can help to improve the accuracy/precision of the image segmentation generated by the hybrid unsupervised and supervised multi-channel segmentation model. Moreover, because such a hybrid unsupervised and supervised multi-channel segmentation model has access to such additional patterns, trends, distributions, and/or relations, the hybrid unsupervised and supervised multi-channel segmentation model can learn more quickly and can thus be trained in significantly less time and/or with significantly less training data than a purely supervised single-channel segmentation model.

In various embodiments, the computerized tool described herein can comprise a receiver component, a probability component, an execution component, and/or a training component.

In various embodiments, the receiver component of the computerized tool can electronically receive and/or otherwise electronically access a CT image. In various cases, the receiver component can electronically retrieve the CT image from any suitable centralized and/or decentralized data structure (e.g., graph data structure, relational data structure, hybrid data structure), whether remote from and/or local to the receiver component. In various other cases, the receiver component can electronically receive the CT image from any suitable medical imaging equipment (e.g., CT imaging system). In various cases, the CT image can depict a vascular structure of a patient, such as a blood vessel, an artery, and/or a lumen. In various other cases, however, the CT image can depict any other suitable anatomical structure (e.g., brain, lung, heart, kidney, intestine, eye, bladder) and/or any suitable portion of an anatomical structure. In various aspects, the CT image can be generated by any suitable CT imaging equipment (e.g., any suitable contrast agent detected by any suitable CT imaging system operating under any suitable clinical protocol). Although the herein disclosure mainly describes CT images and CT imaging equipment, it is to be understood that any other types of anatomical images and/or imaging modalities can be implemented (e.g., CT, contrast-enhanced CT, magnetic resonance imaging (MRI), ultrasound). In various instances, the CT image can be organized as a two-dimensional matrix of pixels with each pixel having an associated HU value and/or as a three-dimensional tensor of voxels with each voxel having an associated HU value. For ease of explanation, the herein disclosure mainly treats the CT image as a two-dimensional matrix of pixels. However, those having ordinary skill in the art will readily understand that the herein teachings are equally applicable to a three-dimensional array of voxels (e.g., a three-dimensional array of voxels can be considered as a sequence of two-dimensional pixel matrices).

In various aspects, it can be desired to segment the CT image according to n classes, for any suitable positive integer n. That is, it can be desired to obtain an image segmentation of the CT image, where the image segmentation indicates, for each pixel, a particular one of n different classes to which the pixel belongs and/or likely belongs. Because the CT image can depict a vascular structure, the n different classes can pertain to such vascular structure. For example, the n different classes can include a vascular wall class (e.g., for pixels that represent the wall of the vascular structure), a calcification class (e.g., for pixels that represent calcified portions of the vascular structure), a blood class (e.g., for pixels that represent blood that is flowing through the vascular structure), and/or a background class (e.g., for pixels that represent something other than the wall, calcification, and/or blood of the vascular structure). As explained herein, the computerized tool can generate such an image segmentation.

In various embodiments, the probability component of the computerized tool can electronically generate n class probability masks by applying an unsupervised modeling technique to the CT image. As a non-limiting example, the unsupervised modeling technique can be Gaussian mixture modeling. More specifically, the probability component can, in various aspects, electronically tabulate a probability distribution of HU values exhibited by the pixels of the CT image. For example, the probability component can define any suitable HU bin size, thereby yielding a particular number of HU bins (e.g., can be based on the HU range exhibited by the CT image). Moreover, the probability component can count the number of pixels in the CT image that fall within each of the HU bins, thereby yielding a frequency distribution of HU values exhibited by the pixels of the CT image, commonly referred to as a histogram. Furthermore, the probability component can compute the probability density of each HU bin by dividing the area of the HU bin by the total area of all of the HU bins, thereby yielding a probability distribution of HU values exhibited by the pixels of the CT image.

In various cases, the probability component can apply Gaussian mixture modeling to the tabulated probability distribution. As those having ordinary skill in the art will appreciate, Gaussian mixture modeling can be considered as an iterative algorithm that utilizes any suitable parameter estimation technique (e.g., expectation maximization, Markov chain Monte Carlo, moment matching, spectral method) to iteratively estimate parameters (e.g., means and/or variances) of multiple Gaussian distributions that sum to a given probability distribution. Therefore, the probability component can leverage Gaussian mixture modeling so as to model the tabulated probability distribution of the CT image as a mixture of n Gaussian distributions. In other words, the probability component can identify the HU means and the HU variances of n different Gaussian distributions that collectively sum to the tabulated probability distribution. Note that the number of Gaussian distributions estimated by the probability component can be equal to the number of segmentation classes (e.g., n classes, n Gaussian distributions, one Gaussian distribution per class). Note, further, that application of Gaussian mixture modeling can be considered as an unsupervised procedure (e.g., Gaussian mixture modeling is an iterative technique to identify component Gaussians of an overall probability distribution, without requiring any annotated training data).

In various aspects, the computerized tool can generate n class probability masks based on the n Gaussian distributions. More specifically, for each pixel in the CT image, the computerized tool can assign to the pixel n probabilities that respectively correspond to the n Gaussian distributions, based on the pixel's HU value. For instance, for every pixel, the probability component can compute a first likelihood that the pixel belongs to the first Gaussian distribution given the pixel's HU value and given the mean and/or variance of the first Gaussian distribution, can compute a second likelihood that the pixel belongs to the second Gaussian distribution given the pixel's HU value and given the mean and/or variance of the second Gaussian distribution, and/or can compute an n-th likelihood that the pixel belongs to the n-th Gaussian distribution given the pixel's HU value and given the mean and/or variance of the n-th Gaussian distribution.

Accordingly, the probability component can output n class probability masks based on these computed probabilities. For example, the probability component can generate a first class probability mask comprising the same number of pixels arranged in the same positions as the CT image, where the value of each pixel in the first class probability mask is equal to and/or otherwise based on that pixel's likelihood of belonging to the first Gaussian distribution. So, pixels that exhibit high values in the first class probability mask can be considered as having high likelihoods of belonging to the first Gaussian distribution, while pixels that exhibit low values in the first class probability mask can be considered as having low likelihoods of belonging to the first Gaussian distribution.

Similarly, the probability component can generate a second class probability mask comprising the same number of pixels arranged in the same positions as the CT image, where the value of each pixel in the second class probability mask is equal to and/or otherwise based on that pixel's likelihood of belonging to the second Gaussian distribution. Thus, pixels that exhibit high values in the second class probability mask can be considered as having high likelihoods of belonging to the second Gaussian distribution, while pixels that exhibit low values in the second class probability mask can be considered as having low likelihoods of belonging to the second Gaussian distribution.

Likewise, the probability component can generate an n-th class probability mask comprising the same number of pixels arranged in the same positions as the CT image, where the value of each pixel in the n-th class probability mask is equal to and/or otherwise based on that pixel's likelihood of belonging to the n-th Gaussian distribution. So, pixels that exhibit high values in the n-th class probability mask can be considered as having high likelihoods of belonging to the n-th Gaussian distribution, while pixels that exhibit low values in the n-th class probability mask can be considered as having low likelihoods of belonging to the n-th Gaussian distribution.

Note that, unlike the CT image, the class probability masks do not exhibit HU values on a pixel-wise basis. Instead, the class probability masks can exhibit probability values on a pixel-wise basis.

Although the above discussion explains how the probability component can generate the n class probability masks when the unsupervised modeling technique is Gaussian mixture modeling, this is a mere non-limiting example. Those having ordinary skill in the art will appreciate that the unsupervised modeling technique can be any other suitable procedure for assigning class probabilities to each pixel in the CT image. Non-limiting examples of such other unsupervised modeling techniques can include fuzzy C-means clustering, K-means clustering, auto-encoder modeling, generative adversarial networks, and/or any other suitable clustering technique that does not require ground truth labels.

In various embodiments, the execution component of the computerized tool can electronically feed the CT image and at least one of the n class probability masks to a deep-learning model, and the deep-learning model can electronically produce as output an image segmentation based on the CT image and based on at least one of the n class probability masks. In various aspects, the deep-learning model can exhibit any suitable neural network architecture. For example, the deep-learning model can include any suitable number of layers, any suitable number of neurons in various layers (e.g., different layers can include different numbers of neurons), any suitable activation functions (e.g., sigmoid, softmax, hyperbolic tangent), and/or any suitable interneuron connectivity patterns (e.g., forward connections, skip connections, recurrent connections). As a non-limiting example, the deep-learning model can exhibit a U-Net architecture (e.g., can have an encoder portion that includes down-sampling layers, and/or can have a decoder portion that includes up-sampling layers). Experimental results confirm that, because the deep-learning model can be configured to receive as input the CT image and at least one of the n class probability masks, rather than the CT image alone, the deep-learning model can, once trained, exhibit better segmentation performance (e.g., better accuracy, higher Dice scores) than a deep-learning model that is configured to receive as input only the CT image. Moreover, experimental results confirm that, because the deep-learning model can be configured to receive as input the CT image and at least one of the n class probability masks, rather than the CT image alone, the deep-learning model can be trained to accurately segment CT images in significantly less time and/or with significantly less training data than a deep-learning model that is configured to receive as input only the CT image.

In various embodiments, if the deep-learning model is not yet trained, the receiver component can electronically access any suitable set of training CT images, and the training component of the computerized tool can electronically train, in a supervised fashion, the deep-learning model based on the set of training CT images. More specifically, it can be the case that each training CT image is annotated with a ground truth segmentation. In various cases, the internal parameters (e.g., weights, biases) of the deep-learning model can be randomly initialized. In various aspects, for each training CT image: the probability component can generate n training class probability masks for the training CT image by leveraging the unsupervised modeling technique; the execution component can feed the both training CT image and at least one of the n training class probability masks to the deep-learning model, thereby yielding an image segmentation of the training CT image; and the training component can apply backpropagation to update the internal parameters of the deep-learning model, based on differences between the image segmentation produced by the deep-learning model and the ground truth annotation of the training CT image. In various cases, the training component can implement batch updating of the internal parameters of the deep-learning model, as desired. Because the deep-learning model can be trained in such a supervised fashion, and because the deep-learning model can be configured to receive as input class probability masks that are generated via the unsupervised modeling technique, the deep-learning model can ultimately be considered as a hybrid unsupervised and supervised image segmentation model.

In summary, the computerized tool described herein can facilitate the creation and/or deployment of a hybrid unsupervised and supervised image segmentation model. Specifically, the computerized tool described herein can train and/or execute a multi-channel deep-learning model, where the multi-channel deep-learning model can exhibit significantly improved segmentation performance as compared to existing single-channel models. In particular, the multi-channel deep-learning model can undergo supervised training, and can be configured to receive as input both a CT image and one or more class probability masks, where the one or more class probability masks can be derived from the CT image via an unsupervised modeling technique (e.g., Gaussian mixture modeling, fuzzy C-means clustering, K-means clustering, auto-encoder modeling, generative adversarial networks). In various cases, the one or more class probability masks can be considered as including contextual information about the pixels in the CT image (e.g., indicating which pixels in the CT image are likely to be related to each other), and such contextual information can have a regularizing effect on the multi-channel deep-learning model. This regularizing effect is not experienced by existing single-channel models whose input is not supplemented with such class probability masks. As a result, the multi-channel deep-learning model can exhibit significantly better segmentation accuracy while simultaneously requiring significantly less training data to achieve such segmentation accuracy.

Various embodiments of the subject innovation can be employed to use hardware and/or software to solve problems that are highly technical in nature (e.g., to facilitate hybrid unsupervised and supervised image segmentation), that are not abstract and that cannot be performed as a set of mental acts by a human. Further, some of the processes performed can be performed by a specialized computer (e.g., deep-learning models, Gaussian mixture modeling) for carrying out defined tasks related to hybrid unsupervised and supervised image segmentation. For example, such defined tasks can include: accessing, by a device operatively coupled to a processor, a computed tomography (CT) image depicting an anatomical structure; generating, by the device and via an unsupervised modeling technique, at least one class probability mask of the anatomical structure based on the CT image; and generating, by the device and via a deep-learning model, an image segmentation based on the CT image and based on the at least one class probability mask. In various aspects, such defined tasks can further include: accessing, by the device, a training CT image; generating, by the device and via the unsupervised modeling technique, at least one training class probability mask based on the training CT image; and training, by the device, the deep-learning model based on the training CT image and based on the at least one training class probability mask.

Such defined tasks are not performed manually by humans. Indeed, neither the human mind nor a human with pen and paper can electronically receive a CT scan, electronically implement an unsupervised modeling technique (e.g., Gaussian mixture modeling) on the HU probability distribution exhibited by the CT scan so as to produce one or more class probability masks, electronically feed both the CT scan and the one or more class probability masks as input to a multi-channel deep-learning segmentation model, and/or electronically train the multi-channel deep-learning segmentation model via backpropagation. Instead, various embodiments of the subject innovation are inherently and inextricably tied to computer technology and cannot be implemented outside of a computing environment (e.g., embodiments of the subject innovation constitute a computerized tool that can utilize unsupervised modeling to train and/or execute a multi-channel deep-learning segmentation model; such a computerized tool cannot be practicably implemented in any sensible way without computers).

Moreover, various embodiments of the subject innovation can integrate into a practical application various teachings described herein relating to the field of image segmentation. As explained above, existing deep-learning models that are configured to produce image segmentations are structured as purely supervised single-channel models. That is, an existing deep-learning model receives as input only the CT scan that is desired to be segmented. In contrast, various embodiments of the subject innovation can include a computerized tool that can train and/or execute a hybrid unsupervised and supervised multi-channel deep-learning model that is configured to produce image segmentations. Such a multi-channel deep-learning model can receive as input both the CT scan that is desired to be segmented and at least one class probability mask, where the computerized tool can electronically derive the at least one class probability mask from the CT scan via an unsupervised modeling technique, such as Gaussian mixture modeling. As explained above, the unsupervised modeling technique can cause the at least one class probability mask to contain patterns, trends, distributions, and/or relations that cannot be readily discerned in the CT scan alone. Thus, since the multi-channel model can receive as input the at least one class probability mask, the multi-channel model can have access to such patterns, trends, distributions, and/or relations, which can enable the multi-channel model to more accurately segment the CT scan and/or to be more quickly trained, thereby requiring less training data. In stark contrast, an existing single-channel model does not receive as input the at least one class probability mask, which can cause the single-channel model to less accurately segment the CT scan and/or to be less quickly trained, thereby requiring more training data. Accordingly, various embodiments of the subject innovation can improve the performance (e.g., segmentation accuracy, training time) of deep-learning segmentation models, which is a concrete and tangible technical improvement, and which clearly constitutes a useful and practical application of computers.

Furthermore, various embodiments of the subject innovation can control real-world tangible devices based on the disclosed teachings. For example, various embodiments of the subject innovation can electronically update parameters of a real-world multi-channel deep-learning segmentation model.

It should be appreciated that the herein figures and description provide non-limiting examples of the subject innovation.

FIG. 1 illustrates a block diagram of an example, non-limiting system 100 that can facilitate hybrid unsupervised and supervised image segmentation in accordance with one or more embodiments described herein.

As shown, a hybrid unsupervised and supervised image segmentation system 102 can have any suitable form of electronic access (e.g., via a wired and/or wireless electronic connection) to a computed tomography image 104 (hereafter "CT image 104"). In various aspects, the CT image 104 can depict any two-dimensional and/or three-dimensional representation of any suitable anatomical structure and/or any suitable portion of an anatomical structure. Various non-limiting examples of such an anatomical structure can include a blood vessel, an artery, a lumen, a brain, a heart, a kidney, an intestine, an eyeball, a lung, and/or a bladder. In various cases, the anatomical structure depicted by the CT image 104 can belong to a human patient. In various other cases, the anatomical structure depicted by the CT image 104 can belong to any other suitable organism (e.g., animal, plant).

In various instances, the CT image 104 can have any suitable data format. For example, the CT image 104 can, in some cases, be formatted as a two-dimensional matrix and/or array of pixels, where each pixel exhibits a corresponding Hounsfield unit (HU) value. As another example, the CT image 104 can, in other cases, be formatted as a three-dimensional tensor and/or array of voxels, where each voxel exhibits a corresponding HU value. For ease of explanation and illustration, the herein disclosure mainly describes the CT image 104 as a two-dimensional matrix of pixels. However, those having ordinary skill in the art will appreciate that the herein teachings can be readily applied to three-dimensional tensors of voxels (e.g., a three-dimensional tensor/array of voxels can be considered as a collective sequence of two-dimensional matrices/arrays of pixels).

In various aspects, the CT image 104 can be electronically generated via any suitable CT imaging equipment and/or imaging system; any suitable contrast agent; any suitable clinical protocol; and/or any suitable reconstruction technique. For example, any suitable slicing and/or reconstruction algorithm can be used to create the CT image 104, any suitable kernel definition can be used to create the CT image 104, and/or any suitable post-processing procedures can be used to augment the CT image 104. As a non-limiting example, the CT image 104 can be a contrast-enhanced coronary computed tomography angiogram (CCTA) image of a vascular structure (e.g., blood vessel) of a patient. Although not explicitly shown in FIG. 1, the herein teachings are not limited only to the CT image 104, but can instead be applied to any other suitable type of image generated by any suitable imaging modality (e.g., CT, contrast-enhanced CT, MRI, ultrasound), as desired.

In various instances, it can be desired to obtain an image segmentation of the CT image 104, where the image segmentation can have the same dimensionality (e.g., same number and/or position of pixels) as the CT image 104. Furthermore, it can be desired that the image segmentation include n classes that are related to and/or otherwise pertinent to the anatomical structure depicted in the CT image 104, for any suitable positive integer n. As explained herein, the hybrid unsupervised and supervised image segmentation system 102 can facilitate such functionality.

In various embodiments, the hybrid unsupervised and supervised image segmentation system 102 can comprise a processor 106 (e.g., computer processing unit, microprocessor) and a computer-readable memory 108 that is operably and/or operatively and/or communicatively connected/coupled to the processor 106. The computer-readable memory 108 can store computer-executable instructions which, upon execution by the processor 106, can cause the processor 106 and/or other components of the hybrid unsupervised and supervised image segmentation system 102 (e.g., receiver component 110, probability component 112, execution component 114) to perform one or more acts. In various embodiments, the computer-readable memory 108 can store computer-executable components (e.g., receiver component 110, probability component 112, execution component 114), and the processor 106 can execute the computer-executable components.

In various embodiments, the hybrid unsupervised and supervised image segmentation system 102 can comprise a receiver component 110. In various aspects, the receiver component 110 can electronically receive and/or otherwise electronically access the CT image 104. In various instances, the receiver component 110 can electronically retrieve the CT image 104 from any suitable database and/or data structure that is electronically accessible to the receiver component 110 (e.g., a graph database, a relational database, a hybrid database), whether such database and/or data structure is remote from and/or local to the receiver component 110. As a non-limiting example, the receiver component 110 can electronically receive the CT image 104 from a CT imaging system (and/or any other suitable computing equipment associated with the CT imaging system) that is deployed in a clinical and/or laboratory setting (e.g., deployed in a hospital). In any case, the receiver component 110 can electronically access the CT image 104, so that other components of the hybrid unsupervised and supervised image segmentation system 102 (e.g., probability component 112, execution component 114) can manipulate and/or otherwise interact with the CT image 104 (e.g., with a copy of the CT image 104).

In various embodiments, the hybrid unsupervised and supervised image segmentation system 102 can comprise a probability component 112. In various aspects, the probability component 112 can electronically generate a set of class probability masks by applying an unsupervised modeling technique to the CT image 104.

More specifically, the probability component 112 can, in various instances, tabulate a frequency distribution of HU values exhibited by the pixels of the CT image 104. In various cases, the probability component 112 can convert this frequency distribution of HU values into a probability distribution of HU values. In various aspects, the probability component 112 can then apply the unsupervised modeling technique to the probability distribution of HU values. As a specific non-limiting example, the unsupervised modeling technique can be Gaussian mixture modeling.

In various instances, Gaussian mixture modeling can be considered as an iterative procedure by which a given probability distribution is decomposed into multiple constituent Gaussian distributions (e.g., multiple bell curves).

That is, application of Gaussian mixture modeling to a given probability distribution can yield estimates of the parameters (e.g., means, variances) of two or more bell curves that add up to the given probability distribution. As those having ordinary skill in the art will appreciate, Gaussian mixture modeling can include any suitable iterative parameter estimation technique to obtain the estimated parameters of the constituent Gaussians, such as expectation maximization, Markov chain Monte Carlo, moment matching, and/or spectral methods.

In various aspects, the probability component 112 can implement Gaussian mixture modeling, thereby causing the probability component 112 to estimate HU means and/or HU variances of n constituent Gaussians that collectively sum to the probability distribution of the HU values exhibited by the CT image 104. That is, the probability component 112 can estimate one constituent Gaussian for each of the n desired segmentation classes. In other cases, however, the probability component 112 can estimate any other suitable number of constituent Gaussians. Moreover, implementation of Gaussian mixture modeling to the probability distribution of HU values exhibited by the CT image 104 can cause the probability component 112 to assign to each pixel of the CT image 104 n probabilities respectively corresponding to the n constituent Gaussians. For instance, for each pixel of the CT image 104, a first of the n probabilities assigned to the pixel can indicate a likelihood that the pixel belongs to the first constituent Gaussian, a second of the n probabilities assigned to the pixel can indicate a likelihood that the pixel belongs to the second constituent Gaussian, and/or an n-th of the n probabilities assigned to the pixel can indicate a likelihood that the pixel belongs to the n-th constituent Gaussian.

In various instances, the probability component 112 can output n class probability masks based on the assigned probabilities generated by the Gaussian mixture modeling. In various cases, a class probability mask can have the same pixel dimensions and/or positions as the CT image 104, but rather than exhibiting pixel-wise HU values, the class probability mask can exhibit pixel-wise probability values indicating likelihood of belonging to a corresponding one of the n constituent Gaussians. For example, the pixels of the first class probability mask can exhibit probabilities of belonging to the first constituent Gaussian, rather than exhibiting HU values. So, pixels in the first class probability mask that have high values (e.g., above any suitable threshold) can be considered as having a high chance of belonging to the first constituent Gaussian, whereas pixels in the first class probability mask that have low values (e.g., below any suitable threshold) can be considered as having a low chance of belonging to the first constituent Gaussian. Similarly, the pixels of the n-th class probability mask can exhibit probabilities of belonging to the n-th constituent Gaussian, rather than exhibiting HU values. So, pixels in the n-th class probability mask that have high values (e.g., above any suitable threshold) can be considered as having a high chance of belonging to the n-th constituent Gaussian, whereas pixels in the n-th class probability mask that have low values (e.g., below any suitable threshold) can be considered as having a low chance of belonging to the n-th constituent Gaussian.

As mentioned above, Gaussian mixture modeling is a mere non-limiting example of the unsupervised modeling technique. In various cases, the unsupervised modeling technique can be any other suitable unsupervised procedure for computing pixel-wise probabilities of belonging to different segmentation classes and/or for otherwise clustering pixels into different segmentation classes (e.g., fuzzy C-means clustering, K-means modeling, auto-encoder modeling, variational auto-encoder modeling, generative adversarial networks).

In various embodiments, the hybrid unsupervised and supervised image segmentation system 102 can comprise an execution component 114. In various aspects, the execution component 114 can electronically execute a deep-learning segmentation model on the CT image 104 and on at least one of the n class probability masks produced by the probability component 112. In other words, the execution component 114 can feed both the CT image 104 and at least one of the n class probability masks as input to the deep-learning segmentation model, and the deep-learning segmentation model can produce as output an image segmentation of the CT image 104.

In various cases, the deep-learning segmentation model can exhibit any suitable artificial neural network architecture. For instance, the deep-learning model can have any suitable number of neural network layers, can have any suitable number of neurons in various layers, can implement any suitable activation functions, and/or can implement any suitable interneuron-connectivity patterns.

In various cases, the deep-learning segmentation model can be trained in any suitable supervised fashion.

Because the deep-learning segmentation model can be trained in a supervised fashion, and because the deep-learning segmentation model can be configured to receive as input both the CT image 104 and at least one of the n class probability masks that are generated by the unsupervised modeling technique, the deep-learning segmentation model can be considered as a hybrid unsupervised and supervised multi-channel model. This is in contrast to existing single-channel models, which are configured to receive as input only the CT image 104 and not at least one of the n class probability masks. In other words, such existing single-channel models do not incorporate a hybrid unsupervised and supervised architecture. As explained herein, since the deep-learning segmentation model is configured to receive as input at least one of the n class probability masks, the deep-learning segmentation model can exhibit improved segmentation accuracy as compared to existing single-channel models. Furthermore, as explained herein, since the deep-learning segmentation model is configured to receive as input at least one of the n class probability masks, the deep-learning segmentation model can be trained with significantly less training data as compared to existing single-channel models.

Figure 2:
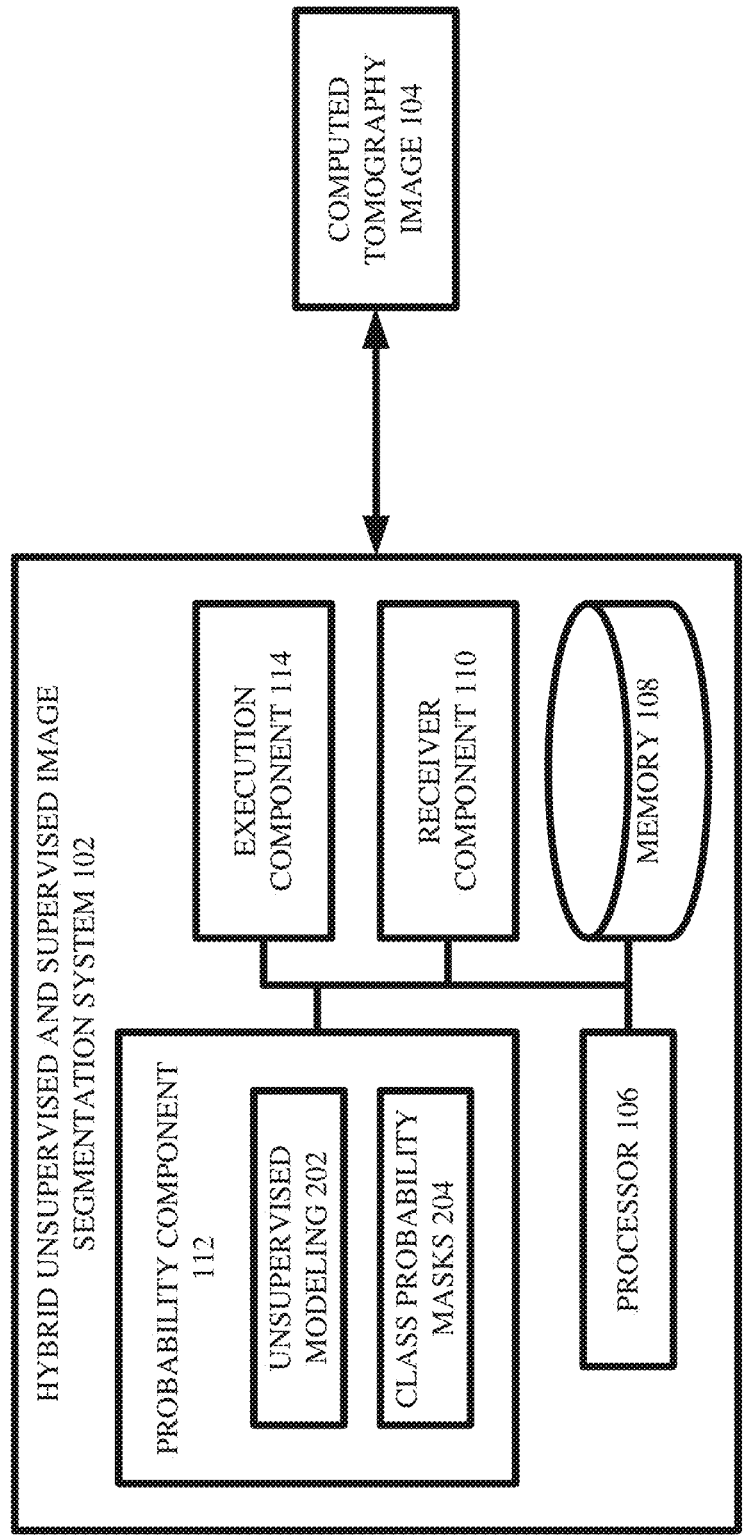
FIG. 2 illustrates a block diagram of an example, non-limiting system including Gaussian mixture modeling and class probability masks that facilitates hybrid unsupervised and supervised image segmentation in accordance with one or more embodiments described herein.

FIG. 2 illustrates a block diagram of an example, non-limiting system 200 including unsupervised model and class probability masks that can facilitate hybrid unsupervised and supervised image segmentation in accordance with one or more embodiments described herein. As shown, the system 200 can, in some cases, comprise the same components as the system 100, and can further comprise unsupervised modeling 202 and/or a set of class probability masks 204.

In various embodiments, the probability component 112 can electronically implement and/or otherwise electronically apply the unsupervised modeling 202 to the CT image 104, thereby yielding the set of class probability masks 204. The unsupervised modeling 202 can, in various embodiments, be Gaussian mixture modeling. As mentioned above, Gaussian mixture modeling can be an iterative technique/procedure for estimating the means and/or variances of two or more Gaussian distributions, which two or more Gaussian distributions sum to a given probability distribution. In other words, when Gaussian mixture modeling is applied to a particular probability distribution, the result can be the identification of any suitable number of bell curves that collectively add together to form the particular probability distribution. Moreover, the result can further include assigning probabilities to each of the data points in the probability distribution, which probabilities indicate likelihoods of belonging to the each of the identified bell curves. In various cases, Gaussian mixture modeling can implement expectation maximization in order to estimate parameters (e.g., means, variances) of the constituent bell curves. In various other cases, however, Gaussian mixture modeling can implement any other suitable parameter estimation technique, such as Markov chain Monte Carlo, moment matching, spectral techniques, and/or any suitable combination thereof.

Accordingly, in various instances, the probability component 112 can tabulate a probability distribution of HU values exhibited by the CT image 104 and can apply Gaussian mixture modeling to such probability distribution. This can cause the probability component 112 to identify n constituent Gaussians that collectively sum to such probability distribution. Once the n constituent Gaussians are identified/estimated, the probability component 112 can compute, for each pixel of the CT image 104, a likelihood of belonging to each of the n constituent Gaussians. In various cases, the probability component 112 can then generate the set of class probability masks 204 based on those pixel-wise likelihoods. Since there can be n segmentation classes, the set of class probability masks 204 can likewise include n class probability masks. This is further explained in non-limiting fashion with respect to FIGS. 3-6.

Figure 3:
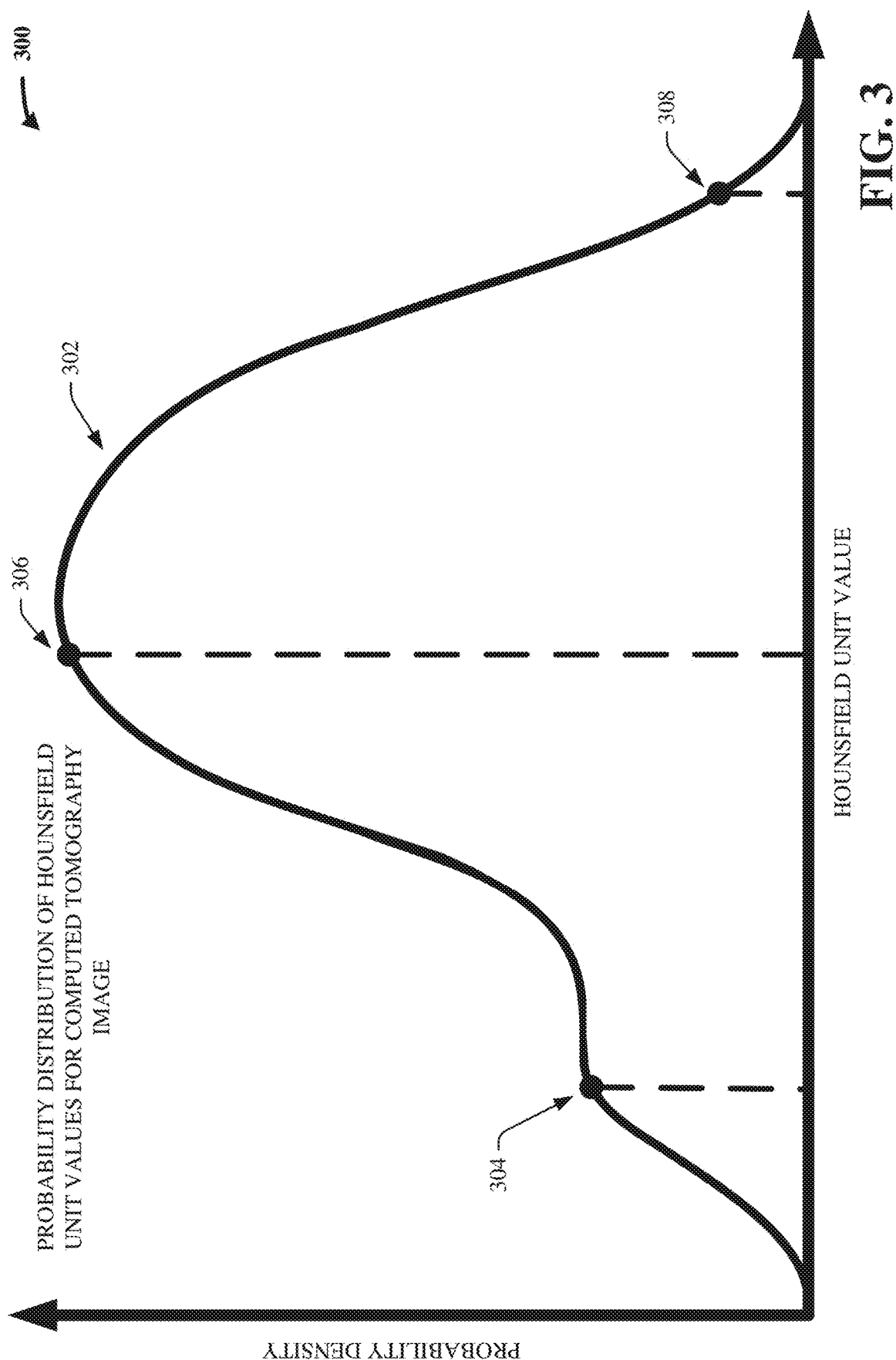
FIG. 3 illustrates an example, non-limiting Hounsfield unit probability distribution exhibited by an example, non-limiting computed tomography image or volume in accordance with one or more embodiments described herein.

FIG. 3 illustrates an example, non-limiting Hounsfield unit probability distribution exhibited by an example, non-limiting computed tomography image in accordance with one or more embodiments described herein.

As explained above, the CT image 104 can be a two-dimensional matrix/array of pixels, where each pixel exhibits an HU value. Alternatively, the CT image 104 can be a three-dimensional array of voxels, where each voxel exhibits an HU value. In any case, the probability component 112 can tabulate a probability distribution of HU values based on the CT image 104. This can be facilitated as follows.

In various instances, the probability component 112 can begin by creating a frequency distribution (e.g., bar graph and/or histogram) of HU values exhibited by the pixels (and/or voxels, as appropriate) of the CT image 104. To create such a frequency distribution of HU values, the probability component 112 can define an HU bin size of any suitable magnitude. Moreover, the probability component 112 can identify an HU range exhibited by the CT image 104. For instance, the HU range can be equal to and/or otherwise based on the difference between the highest HU value of the CT image 104 and the lowest HU value of the CT image 104. Based on the HU bin size and based on the HU range, the probability component 112 can determine a number of HU bins with which to construct the frequency distribution of the CT image 104. In various cases, the number of HU bins can be equal to and/or otherwise based on the quotient obtained by dividing the HU range by the HU bin size. In various aspects, each HU bin can represent a corresponding HU interval in the HU range. In various instances, for each of the HU bins, the probability component 112 can count the number of pixels of the CT image 104 that fall within that HU bin. For example, a pixel can fall within an HU bin if that pixel's HU value is within the HU interval represented by that HU bin. The result of assigning every pixel in the CT image 104 to a corresponding HU bin can be considered as the frequency distribution of the HU values exhibited by the CT image 104.

In various aspects, the probability component 112 can then convert the frequency distribution of HU values into a probability distribution of HU values. For instance, the probability component 112 can transform the frequency and/or cardinality of each HU bin into a probability density by dividing the area of that HU bin (e.g., area can be equal to HU interval multiplied by frequency) by the total area of all the HU bins. The result can be a probability distribution of HU values exhibited by the pixels of the CT image 104.

FIG. 3 illustrates a non-limiting example of such a probability distribution of HU values. As shown in FIG. 3, a graph 300 depicts a probability distribution 302, where the abscissa (e.g., x-axis) of the graph 300 represents HU values and where the ordinate (e.g., y-axis) represents probability densities. In various cases, the probability distribution 302 can be considered as illustrating a probability density of HU values exhibited by the pixels of a non-limiting example embodiment of the CT image 104.

For ease of illustration, the probability distribution 302 is shown as being continuous. However, this is a non-limiting example. Those having ordinary skill in the art will appreciate that, in various cases, a discrete probability distribution can be implemented as desired and/or appropriate.

For purposes of explanation, three points (e.g., 304-308) are called out on the probability distribution 302. The point 304 can represent one or more pixels of the CT image 104 that exhibit a low HU value (e.g., the point 304 is on the left-side and thus low-end of the abscissa) and a low probability density (e.g., the point 304 is on the bottom-side and thus low-end of the ordinate). Furthermore, the point 306 can represent one or more pixels of the CT image 104 that exhibit an intermediate HU value (e.g., the point 306 is in the middle of the abscissa) and a high probability density (e.g., the point 306 is on the top-side and thus high-end of the ordinate). Further still, the point 308 can represent one or more pixels of the CT image 104 that exhibit a high HU value (e.g., the point 308 is on the right-side and thus high-end of the abscissa) and a low probability density (e.g., the point 308 is on the bottom-side and thus low-end of the ordinate). Given the overall shape of the probability distribution 302, the probability distribution 302 can be interpreted as indicating that the CT image 104, in this non-limiting example, includes very many pixels having intermediate-to-upper-intermediate HU values, relatively few pixels with low HU values, and even fewer pixels with high HU values.

In various cases, the probability component 112 can electronically apply the unsupervised modeling 202, which can be Gaussian mixture modeling, to the probability distribution 302.

Figure 4:
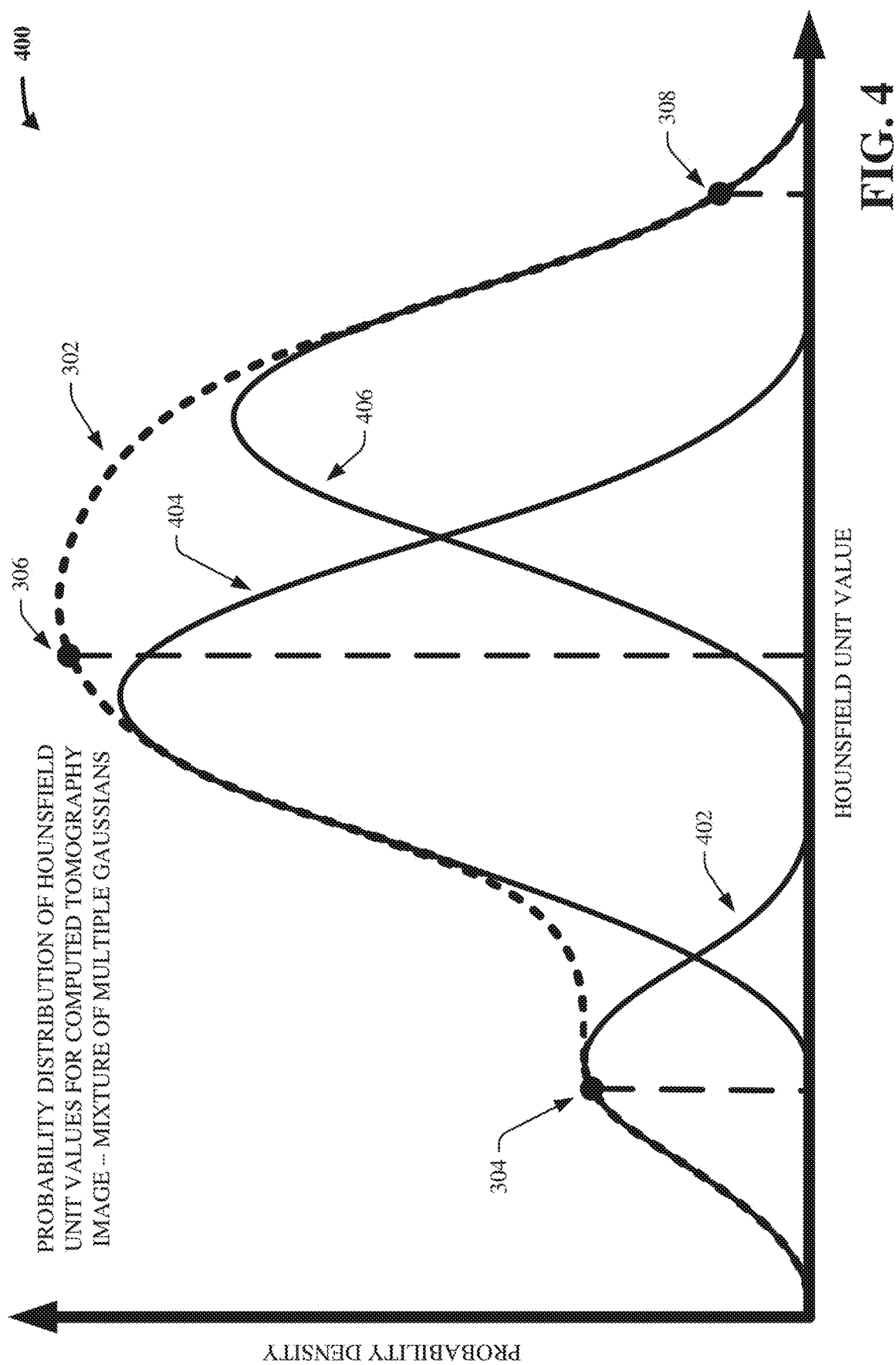
FIG. 4 illustrates how an example, non-limiting Hounsfield unit probability distribution can be the sum of multiple Gaussian distributions in accordance with one or more embodiments described herein.

FIG. 4 illustrates how an example, non-limiting Hounsfield unit probability distribution can be the sum of multiple Gaussian distributions in accordance with one or more embodiments described herein. That is, FIG. 4 shows non-limiting and example results that can be obtained when the probability component 112 electronically applies Gaussian mixture modeling to the probability distribution 302.

For purposes of explanation, suppose that the anatomical structure depicted by the CT image 104 is a blood vessel, and further suppose that there are three segmentation classes: a blood class, a calcification class, and/or a background class. That is, n=3 in this non-limiting example.

As shown in FIG. 4, since n=3, application of Gaussian mixture modeling to the probability distribution 302 can cause the probability component 112 to identify three constituent Gaussians that make up the probability distribution 302: a constituent Gaussian 402, a constituent Gaussian, 404, and/or a constituent Gaussian 406. That is, when the constituent Gaussian 402, the constituent Gaussian 404, and the constituent Gaussian 406 are all added together, the result can be the probability distribution 302. As shown, each of the constituent Gaussians 402-406 can be a bell curve (e.g., Gaussian distribution), meaning that each can be completely defined by a corresponding mean and variance. As mentioned above, application of Gaussian mixture modeling to the probability distribution 302 can cause the probability component 112 to iteratively estimate such means/variances. That is, the probability component 112 can iteratively estimate a first HU mean and a first HU variance for the constituent Gaussian 402, a second HU mean and a second HU variance for the constituent Gaussian 404, and/or a third HU mean and a third HU variance for the constituent Gaussian 406.

In various instances, since n=3 in this non-limiting example, the probability component 112 can assign to each pixel of the CT image 104 three probability values that respectively correspond to the three constituent Gaussians 402-406. More specifically, for each particular pixel, the probability component 112 can identify how far the HU value of the particular pixel is from the mean (e.g., center) of each of the three constituent Gaussians 402-406, and the probability component 112 can use these distances to compute a first probability of the particular pixel belonging to the constituent Gaussian 402, a second probability of the particular pixel belonging to the constituent Gaussian 404, and a third probability of the particular pixel belonging to the constituent Gaussian 406. Moreover, such three probabilities can sum to unity (e.g., each pixel can be assigned to only one of the three constituent Gaussians 402-406, and so the sum of the three probabilities for a given pixel can be 100%). In various cases, the particular pixel can be most likely to belong to the constituent Gaussian whose mean is nearest to the particular pixel. Conversely, the particular pixel can be least likely to belong to the constituent Gaussian whose mean is farthest from the particular pixel. In this way, distance from the mean of each constituent Gaussian can be leveraged to estimate likelihood of belonging to each constituent Gaussian.

For example, suppose that a particular pixel has an HU value that matches that of the point 304 (e.g., a low HU value). In such case, that particular pixel can be assigned three probabilities: a first probability indicating the likelihood that the particular pixel belongs to the constituent Gaussian 402, a second probability indicating the likelihood that the particular pixel belongs to the constituent Gaussian 404, and/or a third probability indicating the likelihood that the particular pixel belongs to the constituent Gaussian 406. In various cases, these three probabilities can be based on the distance between the HU value at the point 304 and the HU mean of the constituent Gaussian 402, based on the distance between the HU value at the point 304 and the HU mean of the constituent Gaussian 404, and based on the distance between the HU value at the point 304 and the HU mean of the constituent Gaussian 406. Moreover, these three probabilities can sum to unity. As shown, the point 304 is very near to the mean of the constituent Gaussian 402, is quite far from the mean of the constituent Gaussian 404, and is even farther from the mean of the constituent Gaussian 406. Accordingly, the first probability can be quite high, while the second probability can be quite small, and the third probability can be even smaller still. In other words, these three probabilities can indicate that the particular pixel can be very likely to belong to the constituent Gaussian 402 and can be very unlikely to belong to either of the constituent Gaussians 404 or 406.

As another example, suppose that a particular pixel has an HU value that matches that of the point 306 (e.g., an intermediate HU value). In such case, that particular pixel can be assigned three probabilities: a first probability indicating the likelihood that the particular pixel belongs to the constituent Gaussian 402, a second probability indicating the likelihood that the particular pixel belongs to the constituent Gaussian 404, and/or a third probability indicating the likelihood that the particular pixel belongs to the constituent Gaussian 406. In various cases, these three probabilities can be based on the distance between the HU value at the point 306 and the HU mean of the constituent Gaussian 402, based on the distance between the HU value at the point 306 and the HU mean of the constituent Gaussian 404, and based on the distance between the HU value at the point 306 and the HU mean of the constituent Gaussian 406. Also, these three probabilities can sum to unity. As shown, the point 306 is quite close to the mean of the constituent Gaussian 404, is somewhat far from the mean of the constituent Gaussian 406, and is even farther from the mean of the constituent Gaussian 402. Accordingly, the second probability can be quite high, while the third probability can be quite small, and the first probability can be even smaller. In other words, these three probabilities can indicate that the particular pixel can be very likely to belong to the constituent Gaussian 404 and can be very unlikely to belong to either of the constituent Gaussians 402 or 406.

As yet another example, suppose that a particular pixel has an HU value that matches that of the point 308 (e.g., a high HU value). In such case, that particular pixel can be assigned three probabilities: a first probability indicating the likelihood that the particular pixel belongs to the constituent Gaussian 402, a second probability indicating the likelihood that the particular pixel belongs to the constituent Gaussian 404, and/or a third probability indicating the likelihood that the particular pixel belongs to the constituent Gaussian 406. In various cases, these three probabilities can be based on the distance between the HU value at the point 308 and the HU mean of the constituent Gaussian 402, based on the distance between the HU value at the point 308 and the HU mean of the constituent Gaussian 404, and based on the distance between the HU value at the point 308 and the HU mean of the constituent Gaussian 406. Moreover, these three probabilities can sum to unity. As shown, the point 308 is closest to the mean of the constituent Gaussian 406, is far from the mean of the constituent Gaussian 404, and is even farther from the mean of the constituent Gaussian 402. Accordingly, the third probability can be quite high, while the second probability can be quite small, and the first probability can be smaller still. In other words, these three probabilities can indicate that the particular pixel can be very likely to belong to the constituent Gaussian 406 and can be very unlikely to belong to either of the constituent Gaussians 402 or 404.

In various aspects, the probability component 112 can generate the set of class probability masks 204 based on the above-mentioned computed probabilities. Since n=3 in this non-limiting example, the set of class probability masks 204 can include three class probability masks. The first class probability mask can have the same dimensions (e.g., same number and/or positions of pixels) as the CT image 104. But rather than exhibiting pixel-wise (and/or voxel-wise) HU values, the first class probability mask can exhibit pixel-wise probabilities of belonging to the constituent Gaussian 402.

Accordingly, pixels that exhibit high values in the first class probability mask can be considered as having high chances of belonging to the constituent Gaussian 402, while pixels that exhibit low values in the first class probability mask can be considered as having low chances of belonging to the constituent Gaussian 402. Similarly, the second class probability mask can have the same dimensions (e.g., same number and/or positions of pixels) as the CT image 104. But rather than exhibiting pixel-wise HU values, the second class probability mask can exhibit pixel-wise probabilities of belonging to the constituent Gaussian 404. Thus, pixels that exhibit high values in the second class probability mask can be considered as having high chances of belonging to the constituent Gaussian 404, while pixels that exhibit low values in the second class probability mask can be considered as having low chances of belonging to the constituent Gaussian 404. Likewise, the third class probability mask can have the same dimensions (e.g., same number and/or positions of pixels) as the CT image 104. But rather than exhibiting pixel-wise HU values, the third class probability mask can exhibit pixel-wise probabilities of belonging to the constituent Gaussian 406. So, pixels that exhibit high values in the third class probability mask can be considered as having high chances of belonging to the constituent Gaussian 406, while pixels that exhibit low values in the third class probability mask can be considered as having low chances of belonging to the constituent Gaussian 406.

Figure 5:
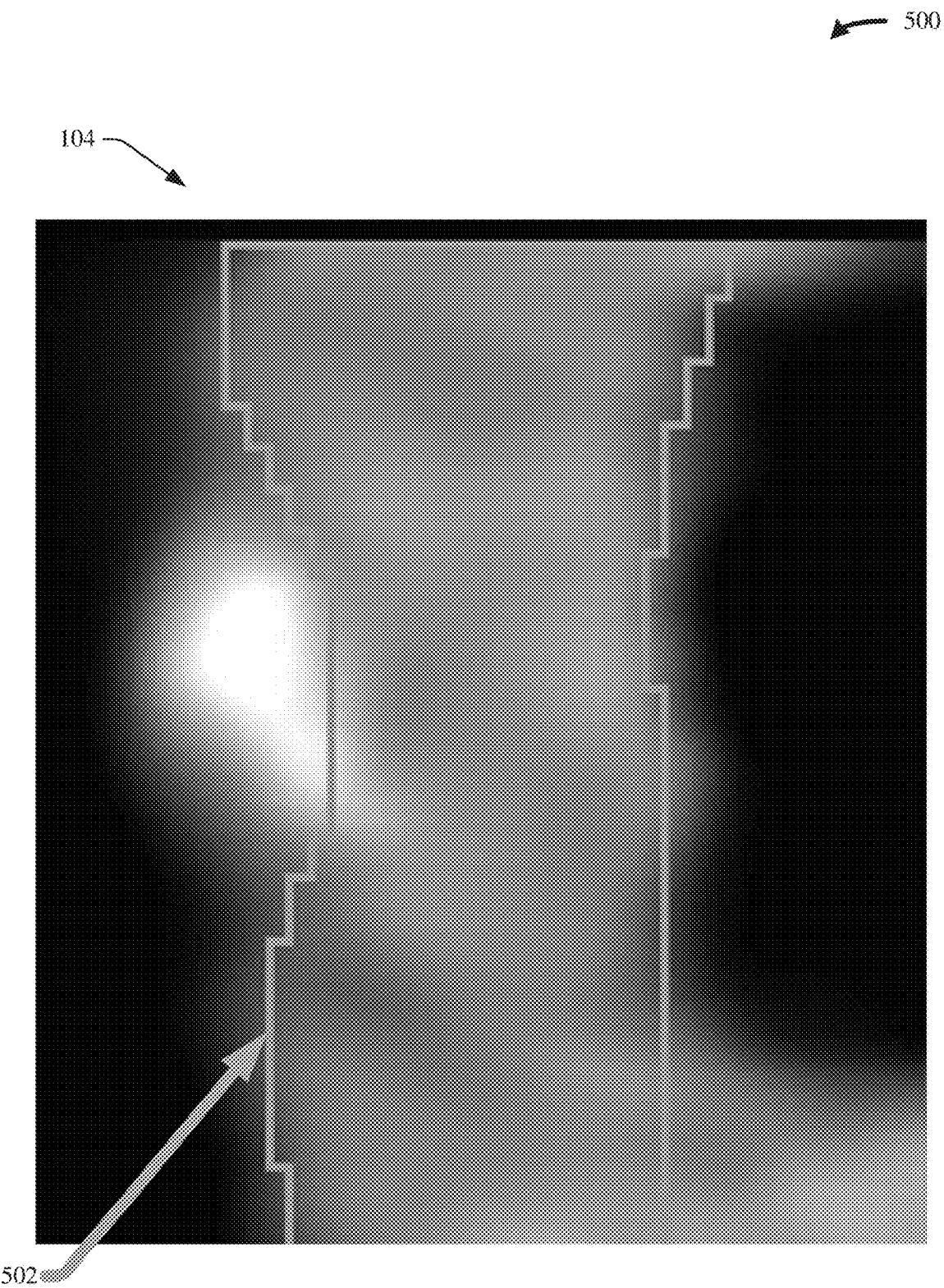
FIG. 5 illustrates an example, non-limiting computed tomography image in accordance with one or more embodiments described herein.

FIG. 5 illustrates an example, non-limiting computed tomography image 500 in accordance with one or more embodiments described herein. In other words, FIG. 5 illustrates a non-limiting embodiment of the CT image 104. As shown, in the non-limiting example of FIG. 5, the CT image 104 can be a two-dimensional matrix of pixels that depicts a portion of a patient's anatomy including a blood vessel. In various instances, as shown, the CT image 104 can include various pixels that are dark in color, various pixels that are various shades of gray in color, and/or various pixels that are bright in color. Pixels that are dark in color can be considered as having low HU values, pixels that are gray in color can be considered as having intermediate HU values, and/or pixels that are bright in color can be considered as having high HU values. In various aspects, the gray pixels can represent blood flowing through the blood vessel, the white pixels can represent calcification present in the blood vessel, and the black pixels can represent a background of the blood vessel. As those having ordinary skill in the art will appreciate, the color appearance of these features can be modified by changing characteristics of the function that maps HU value to gray-scale color value. For viewing convenience only, a boundary 502 is superimposed over the CT image 104 to show where blood can flow through the blood vessel. Note that the boundary 502 is included only as an explanatory tool for purposes of this disclosure; the boundary 502 is not part of the CT image 104 and thus is not received/analyzed by any deep-learning models described herein.

In various cases, it can be desired to segment the CT image 104 shown in FIG. 5 according to three (e.g., n=3) segmentation classes: a blood class, a calcification class, and/or a background class. Prior to generating such an image segmentation, the probability component 112 can apply the unsupervised modeling 202 (e.g., Gaussian mixture modeling) to the CT image 104 as described above, thereby generating the set of class probability masks 204. Since n=3 in this non-limiting example, there can be n=3 class probability masks in the set of class probability masks 204, as shown in FIG. 6.

Figure 6:
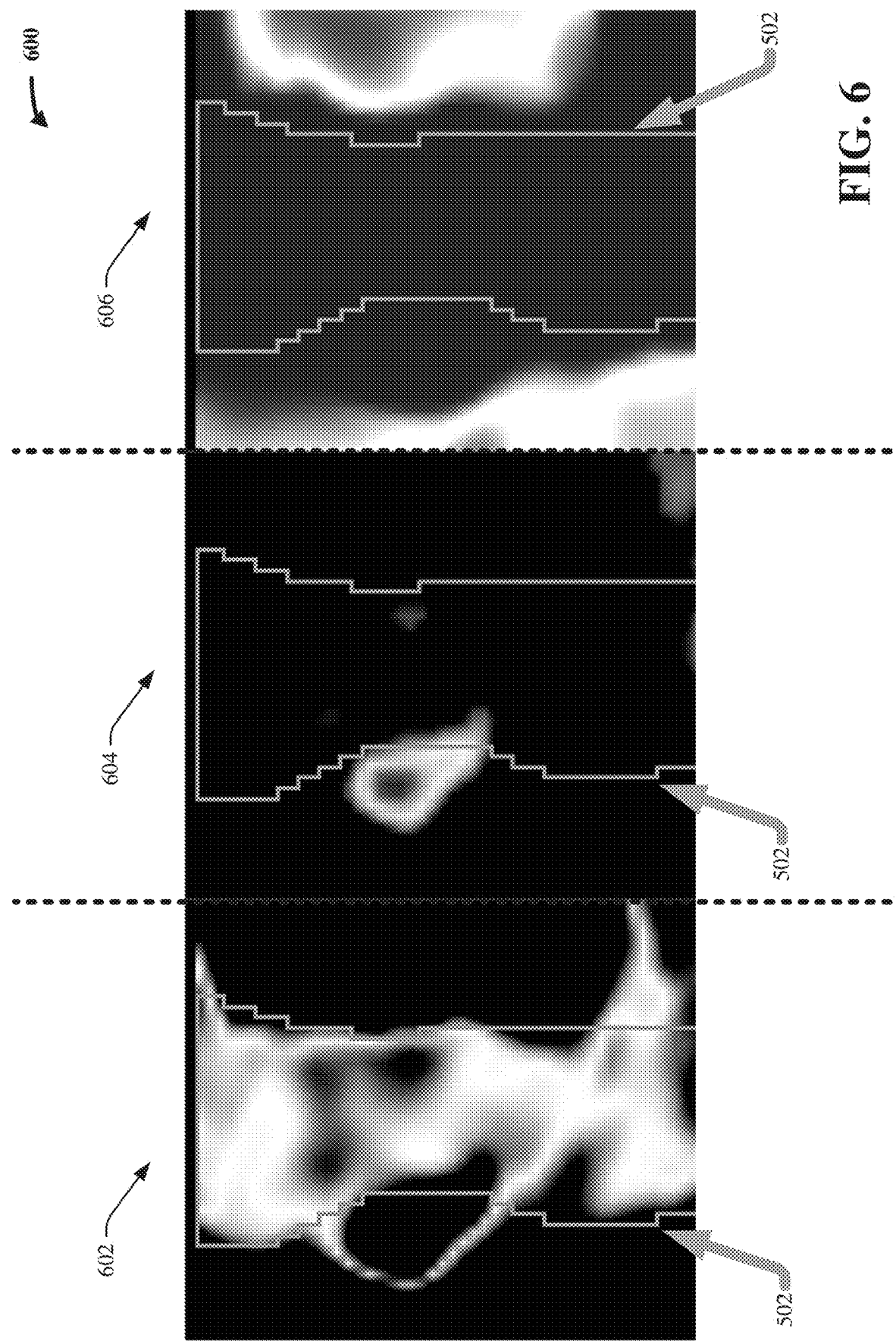
FIG. 6 illustrates example, non-limiting class probability masks generated via Gaussian mixture modeling in accordance with one or more embodiments described herein.

FIG. 6 illustrates example, non-limiting class probability masks 600 generated via Gaussian mixture modeling in accordance with one or more embodiments described herein. That is, FIG. 6 shows a non-limiting embodiment of the set of class probability masks 204 that can be generated by the probability component 112 based on the non-limiting example of the CT image 104 depicted in FIG. 5.

As shown in FIG. 6, the set of class probability masks 204 can include three class probability masks: 602-606. As shown, each of the class probability masks 602-606 can have the same dimensionality as the CT image 104 that is depicted in FIG. 5. In other words, each of the class probability masks 602-606 can have the same number of pixels arranged in the same positions as the CT image 104. Again, for viewing convenience only, the boundary 502 is superimposed on each of the class probability masks 602-606, so as to help orient the reader.

In various instances, rather than exhibiting pixel-wise HU values, each of the class probability masks 602-606 can exhibit pixel-wise probability values that respectively correspond to n=3 constituent Gaussians iteratively estimated by the probability component 112 via Gaussian mixture modeling. More specifically, the class probability mask 602 can exhibit pixel-wise probabilities indicating likelihood of belonging to a constituent Gaussian A identified by the probability component 112, the class probability mask 604 can exhibit pixel-wise probabilities indicating likelihood of belonging to a constituent Gaussian B identified by the probability component 112, and/or the class probability mask 606 can exhibit pixel-wise probabilities indicating likelihood of belonging to a constituent Gaussian C identified by the probability component 112.

So, the higher a pixel's value is (e.g., the brighter the pixel is) in the class probability mask 602, the more likely it is that the pixel belongs to the constituent Gaussian A. On the other hand, the lower a pixel's value is (e.g., the darker the pixel is) in the class probability mask 602, the less likely it is that the pixel belongs to the constituent Gaussian A. In other words, the class probability mask 602 can be interpreted as indicating that the brightly-colored pixels in the class probability mask 602 are likely to belong in the same segmentation class as each other. As recognizable by a medical expert, it can be the case that the constituent Gaussian A represents and/or otherwise corresponds to the blood segmentation class. After all, the brightly-colored pixels in the class probability mask 602 are the same pixels that are colored in various shades of gray in FIG. 5, and such gray pixels in FIG. 5 can represent blood within the depicted blood vessel. Accordingly, the class probability mask 602 can, in various instances, be considered as a blood class probability mask.

Similarly, the higher a pixel's value is (e.g., the brighter the pixel is) in the class probability mask 604, the more likely it is that the pixel belongs to the constituent Gaussian B. On the other hand, the lower a pixel's value is (e.g., the darker the pixel is) in the class probability mask 604, the less likely it is that the pixel belongs to the constituent Gaussian B. In other words, the class probability mask 604 can be interpreted as indicating that the brightly-colored pixels in the class probability mask 604 are likely to belong in the same segmentation class as each other. As recognizable by a medical expert, it can be the case that the constituent Gaussian B represents and/or otherwise corresponds to the calcification segmentation class. After all, the brightly-colored pixels in the class probability mask 604 are the same pixels that are brightly-colored in FIG. 5, and such brightly-colored pixels in FIG. 5 can represent calcified portions of the depicted blood vessel. Accordingly, the class probability mask 604 can, in various instances, be considered as a calcification class probability mask.

Likewise, the higher a pixel's value is (e.g., the brighter the pixel is) in the class probability mask 606, the more likely it is that the pixel belongs to the constituent Gaussian C. On the other hand, the lower a pixel's value is (e.g., the darker the pixel is) in the class probability mask 606, the less likely it is that the pixel belongs to the constituent Gaussian C. In other words, the class probability mask 606 can be interpreted as indicating that the brightly-colored pixels in the class probability mask 606 are likely to belong in the same segmentation class as each other. As recognizable by a medical expert, it can be the case that the constituent Gaussian C represents and/or otherwise corresponds to the background segmentation class. After all, the brightly-colored pixels in the class probability mask 606 are the same pixels that are darkly-colored in FIG. 5, and such darkly-colored pixels in FIG. 5 can represent the background outside of the depicted blood vessel. Accordingly, the class probability mask 606 can, in various instances, be considered as a background class probability mask.

Although the above discussion mainly explains how the probability component 112 can generate the class probability masks 204 via the unsupervised modeling 202 when the unsupervised modeling 202 is Gaussian mixture modeling, this is a mere non-limiting example. Those having ordinary skill in the art will appreciate that the unsupervised modeling 202 can, in various embodiments, be any other suitable procedure for generating the class probability masks 204. As some non-limiting examples, the unsupervised modeling 202 can be fuzzy C-means clustering, K-means clustering, auto-encoder modeling, variational auto-encoder modeling, generative adversarial networks, and/or any other suitable unsupervised clustering technique.

Figure 7:
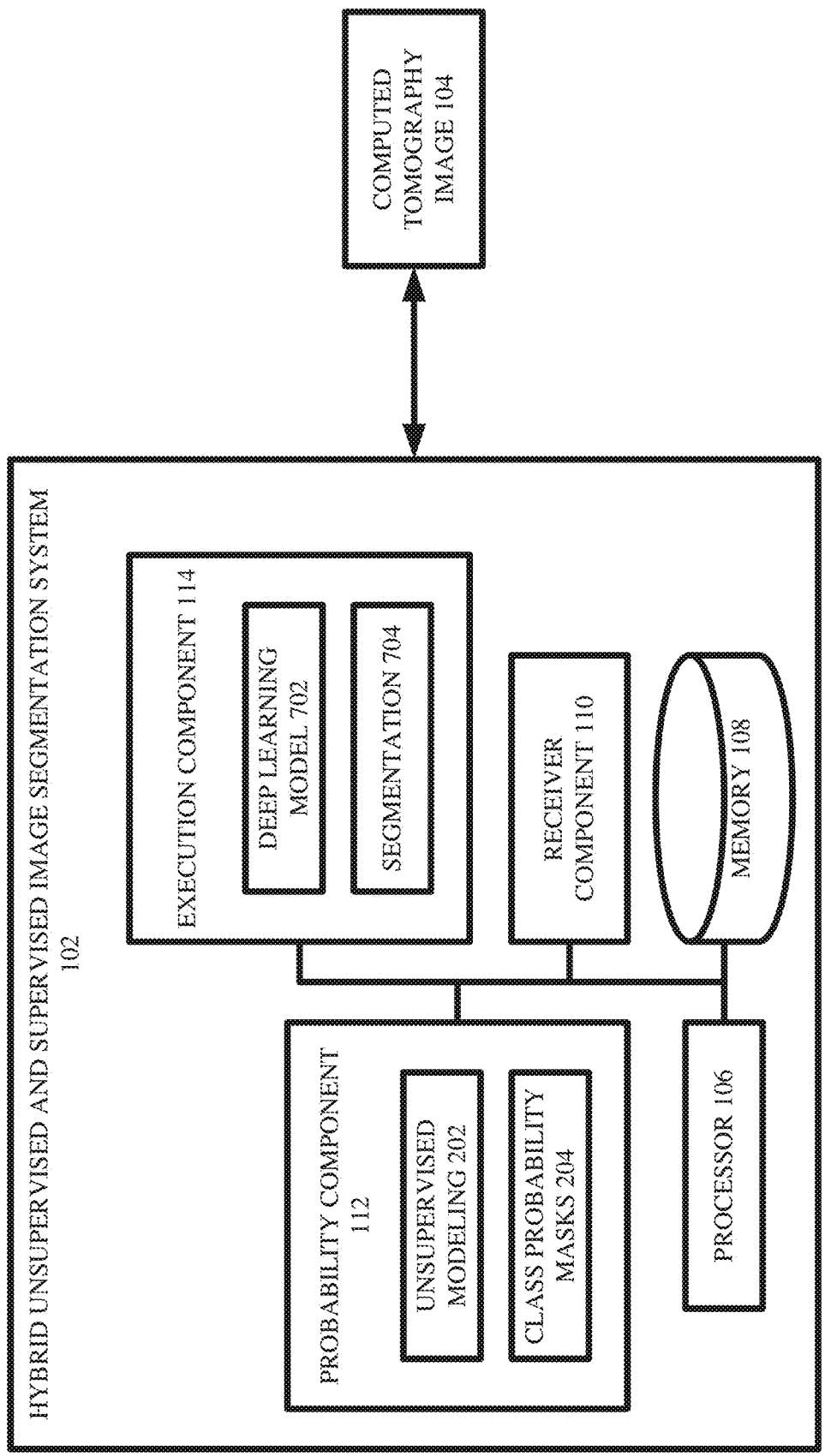
FIG. 7 illustrates a block diagram of an example, non-limiting system including a deep-learning model and a segmentation that facilitates hybrid unsupervised and supervised image segmentation in accordance with one or more embodiments described herein.

FIG. 7 illustrates a block diagram of an example, non-limiting system 700 including a deep-learning model and a segmentation that can facilitate hybrid unsupervised and supervised image segmentation in accordance with one or more embodiments described herein. As shown, the system 700 can, in some cases, comprise the same components as the system 200, and can further comprise a deep-learning model 702 and/or a segmentation 704.

In various embodiments, the execution component 114 can electronically feed as input both the CT image 104 and at least one of the set of class probability masks 204 to the deep-learning model 702. In various aspects, the deep-learning model 702 can then generate the segmentation 704, based on both the CT image 104 and the set of class probability masks 204. In various cases, the segmentation 704 can be any suitable image segmentation of the CT image 104. That is, the segmentation 704 can be a pixel-wise mask that indicates to which of the n segmentation classes each pixel of the CT image 104 belongs.

In various instances, the deep-learning model 702 can exhibit any suitable artificial neural network architecture. That is, the deep-learning model 702 can include any suitable number of neural network layers, can include any suitable number of neurons in various layers (e.g., different layers can have different numbers of neurons), can include any suitable activation functions (e.g., softmax, sigmoid, hyperbolic tangent, rectified linear unit), and/or can include any suitable interneuron connectivity patterns (e.g., forward connections, skip connections, recurrent connections). In some cases, the deep-learning model 702 can exhibit a U-Net architecture, including an encoder portion (e.g., one or more down-sampling layers) and a decoder portion (e.g., one or more up-sampling layers).

Although the deep-learning model 702 is depicted in FIG. 7 as being local to the execution component 114, this is merely a non-limiting example. In various instances, the deep-learning model 702 can be remote from the execution component 114 and/or the hybrid unsupervised and supervised image segmentation system 102.

Figure 8:
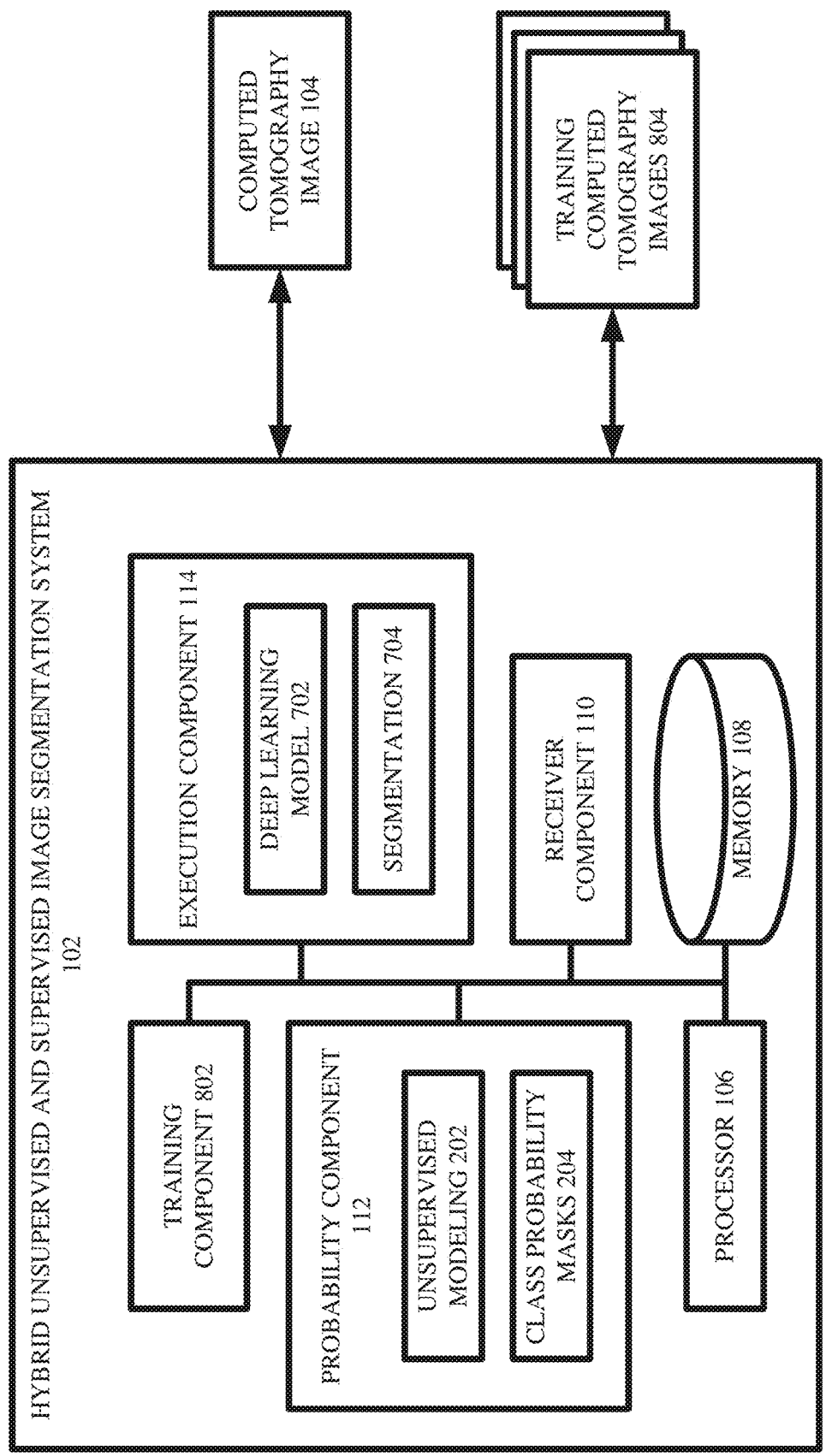
FIG. 8 illustrates a block diagram of an example, non-limiting system including a training component that facilitates hybrid unsupervised and supervised image segmentation in accordance with one or more embodiments described herein.

FIG. 8 illustrates a block diagram of an example, non-limiting system 800 including a training component that can facilitate hybrid unsupervised and supervised image segmentation in accordance with one or more embodiments described herein. As shown, the system 800 can, in some cases, comprise the same components as the system 700, and can further comprise a training component 802 and/or a set of training computed tomography images 804 (hereafter "set of training CT images 804").

In various aspects, it can be the case that the segmentation 704 is not an accurate image segmentation of the CT image 104, if the deep-learning model 702 has not yet been trained. Accordingly, in various instances, the receiver component 110 can electronically access the set of training CT images 804 from any suitable data structure, and the training component 802 can electronically train the deep-learning model 702 based on the set of training CT images 804. More specifically, the set of training CT images 804 can include any suitable number of training CT images, where each training CT image in the set of training CT images 804 can have the same dimensionality as the CT image 104. Moreover, each training CT image in the set of training CT images 804 can be annotated with a ground truth image segmentation. Accordingly, the training component 802 can facilitate supervised training of the deep-learning model 702, based on the set of training CT images 804.

For example, the parameters (e.g., weights and/or biases) of the deep-learning model 702 can be randomly initialized. In various cases, for each training CT image in the set of training CT images 804, the following can occur: the probability component 112 can apply the unsupervised modeling 202 (e.g., Gaussian mixture modeling) to the training CT image, thereby yielding n training class probability masks; the execution component 114 can feed both the training CT image and at least one of the n training class probability masks to the deep-learning model 702, thereby causing the deep-learning model 702 to output an image segmentation corresponding to the training CT image; and the training component 802 can update, via backpropagation, the parameters of the deep-learning model 702 based on a difference (e.g., loss, error) between the image segmentation produced by the deep-learning model 702 and the ground truth image segmentation corresponding to the training CT image. By repeating this procedure for all (e.g., and/or fewer than all, in some cases) of the set of training CT images 804, the parameters of the deep-learning model 702 can be optimized to produce sufficiently accurate image segmentations. As those having ordinary skill in the art will appreciate, the training component 802 can, in some cases, implement batch updating of the parameters of the deep-learning model 702, as desired.

In various embodiments, because the deep-learning model 702 can be configured to receive as input both the CT image 104 and at least one of the set of class probability masks 204, and because the set of class probability masks 204 can be derived via the unsupervised modeling 202, the deep-learning model 702 can be considered as a hybrid unsupervised and supervised multi-channel segmentation model. In stark contrast, a deep-learning model that is configured to receive as input only the CT image 104 would be considered as a purely supervised single-channel segmentation model. The inventors of various embodiments of the subject innovation experimentally verified that a hybrid unsupervised and supervised multi-channel segmentation model as described herein can exhibit greatly improved segmentation accuracy as compared to a purely supervised single-channel segmentation model. Moreover, the inventors of various embodiments of the subject innovation further experimentally verified that a hybrid unsupervised and supervised multi-channel segmentation model as described herein can exhibit greatly reduced training time as compared to a purely supervised single-channel segmentation model.

Specifically, the inventors configured a hybrid unsupervised and supervised multi-channel segmentation model as described herein to perform image segmentation of CT scans depicting lumina, where the unsupervised modeling 202 was Gaussian mixture modeling. Furthermore, the inventors validated the hybrid unsupervised and supervised multi-channel segmentation model using a coronary CT dataset of 36 patients from a particular medical site with invasive pressure measurement. The lumina were manually segmented for ground-truth creation. In addition to the hybrid unsupervised and supervised multi-channel segmentation model, the inventors also configured a single-channel segmentation model. The hybrid unsupervised and supervised multi-channel segmentation model was configured to receive as input both a CT scan and one or more class probability masks derived from the CT scan via Gaussian mixture modeling. In contrast, the single-channel segmentation model was configured to receive as input only a CT scan. However, both models utilized an encoder-decoder neural network architecture (e.g., U-Net). For comparison, a holdout of 6 datasets was used for testing for both models. The hybrid unsupervised and supervised multi-channel segmentation model was trained with 20% less data (24 datasets) compared to 30 datasets used to train the single-channel segmentation model. With a statistical significance level of p<0.05, the inventors found that the Dice similarity coefficient of the hybrid unsupervised and supervised multi-channel segmentation model was about 0.84, while the Dice similarity coefficient of the single-channel segmentation model was about 0.81. Those having ordinary skill in the art will appreciate that this means that the hybrid unsupervised and supervised multi-channel segmentation model exhibited a significant improvement in segmentation performance as compared to the single-channel segmentation model. Furthermore, it must be emphasized that the hybrid unsupervised and supervised multi-channel segmentation model achieved this marked performance improvement while having been trained with 20% less data than the single-channel segmentation model. In other words, not only did the hybrid unsupervised and supervised multi-channel segmentation model learn to segment CT scans more accurately, but the hybrid unsupervised and supervised multi-channel segmentation model also required less training to achieve such higher accuracy. Furthermore, the inventors observed that the hybrid unsupervised and supervised multi-channel segmentation model was less dependent on differences and/or variations in reconstructed HU values, as compared to the single-channel segmentation model, which suggests that the hybrid unsupervised and supervised multi-channel segmentation model generalized more completely than the single-channel segmentation model. Accordingly, various embodiments of the subject innovation certainly constitute concrete and tangible technical improvements in the field of image segmentation.

Figure 9:
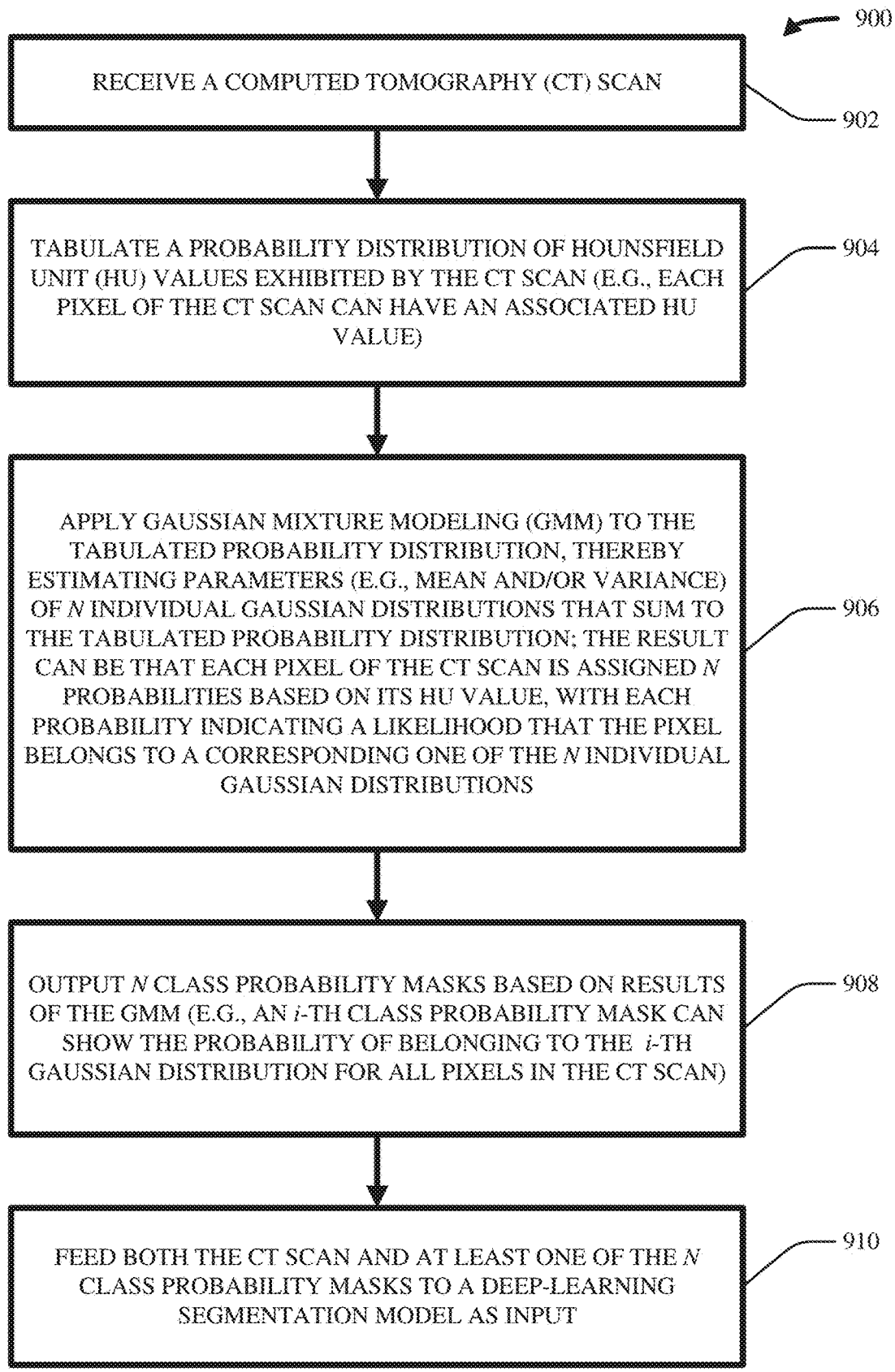
FIG. 9 illustrates a flow diagram of an example, non-limiting computer-implemented method that facilitates hybrid unsupervised and supervised image segmentation in accordance with one or more embodiments described herein.

FIG. 9 illustrates a flow diagram of an example, non-limiting computer-implemented method 900 that can facilitate hybrid unsupervised and supervised image segmentation in accordance with one or more embodiments described herein. In various cases, the computer-implemented method 900 can be facilitated by the hybrid unsupervised and supervised image segmentation system 102.

In various embodiments, act 902 can include receiving, by a device (e.g., 110) operatively coupled to a processor, a computed tomography (CT) scan (e.g., 104).

In various aspects, act 904 can include tabulating, by the device (e.g., 112), a probability distribution (e.g., 302) of Hounsfield unit (HU) values exhibited by the CT scan. In various cases, each pixel of the CT scan can have an associated HU value, and so a frequency distribution, and thus a probability distribution, of such pixel-wise HU values can be tabulated.

In various instances, act 906 can include applying, by the device (e.g., 112), Gaussian mixture modeling (e.g., an embodiment of 202) to the tabulated probability distribution, thereby estimating parameters (e.g., mean and/or variance) of n individual Gaussian distributions (e.g., 402, 404, 406) that sum to the tabulated probability distribution, for any suitable positive integer n. In various cases, the result can be that each pixel of the CT scan is assigned n probabilities based on the pixel's HU value, with each probability indicating a likelihood that the pixel belongs to a corresponding one of the n individual Gaussian distributions.

In various aspects, act 908 can include outputting, by the device (e.g., 112), n class probability masks (e.g., 204, and/or 602-606) based on results of the Gaussian mixture modeling. In various cases, an i-th class probability mask, for $1 \leq i \leq n$, can show the probability of belonging to the i-th Gaussian distribution for all pixels in the CT scan.

In various instances, act 910 can include feeding, by the device (e.g., 114), both the CT scan and at least one of the n class probability masks to a deep-learning segmentation model (e.g., 702) as input. If the deep-learning segmentation model has been trained, the deep-learning segmentation model can output an image segmentation (e.g., 704) based on the CT scan and based on the n class probability masks.

Figure 10:
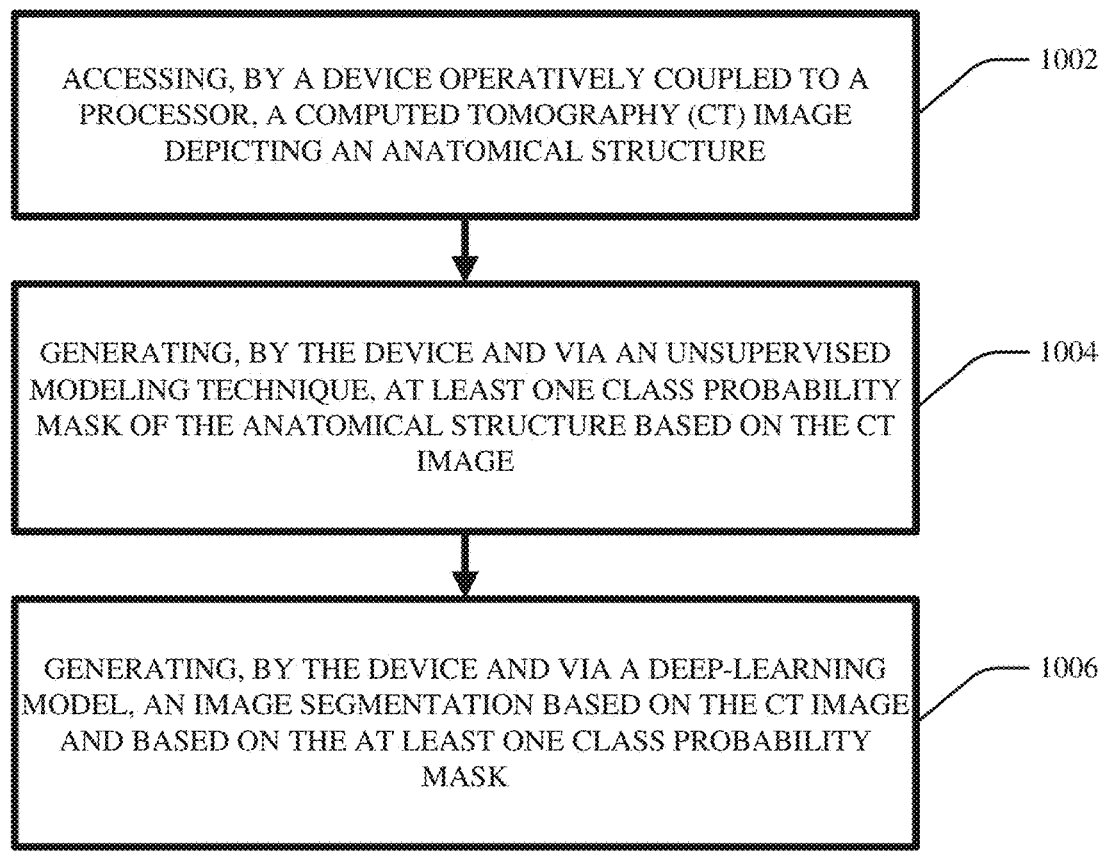
FIG. 10 illustrates a flow diagram of an example, non-limiting computer-implemented method that facilitates hybrid unsupervised and supervised image segmentation in accordance with one or more embodiments described herein.

FIG. 10 illustrates a flow diagram of an example, non-limiting computer-implemented method 1000 that can facilitate hybrid unsupervised and supervised image segmentation in accordance with one or more embodiments described herein. In various cases, the hybrid unsupervised and supervised image segmentation system 102 can facilitate the computer-implemented method 1000.

In various embodiments, act 1002 can include accessing, by a device (e.g., 110) operatively coupled to a processor, a computed tomography (CT) image (e.g., 104) depicting an anatomical structure.

In various aspects, act 1004 can include generating, by the device (e.g., 112) and via an unsupervised modeling technique (e.g., 202), at least one class probability mask (e.g., 204) of the anatomical structure based on the CT image.

In various instances, act 1006 can include generating, by the device (e.g., 114) and via a deep-learning model (e.g., 702), an image segmentation (e.g., 704) based on the CT image and based on the at least one class probability mask.

Although not explicitly shown in FIG. 10, the computer-implemented method 1000 can further comprise: accessing, by the device (e.g., 110), a training CT image (e.g., one of 804); generating, by the device (e.g., 112) and via unsupervised modeling technique, at least one training class probability mask based on the training CT image; and training, by the device (e.g., 802), the deep-learning model based on the training CT image and based on the at least one training class probability mask.

Although not explicitly shown in FIG. 10, the unsupervised modeling technique can be Gaussian mixture modeling, fuzzy C-means clustering, K-means clustering, a generative adversarial network, and/or an auto-encoder.

Although not explicitly shown in FIG. 10, the deep-learning model can exhibit a U-Net architecture that includes an encoder portion and a decoder portion.

Although not explicitly shown in FIG. 10, the anatomical structure can be a vascular structure.

Although not explicitly shown in FIG. 10, the vascular structure can be a lumen, and the at least one class probability mask can include a blood class probability mask (e.g., 602), a plaque calcification class probability mask (e.g., 604), or a background class probability mask (e.g., 606).

Although the herein disclosure mainly describes various embodiments of the subject innovation where the CT image 104 is a two-dimensional matrix of pixels, this is a mere non-limiting example. Those having ordinary skill in the art will appreciate that the CT image 104 can have any other suitable dimensionality. For instance, in some cases, the CT image 104 can be a three-dimensional tensor of voxels, rather than a two-dimensional matrix of pixels. In any case, those having ordinary skill in the art will understand that the herein teachings can be readily applied, regardless of the dimensionality of the CT image 104. Those having ordinary skill in the art will further understand that, if the CT image 104 is a three-dimensional tensor of voxels, the segmentation 704 can likewise be a three-dimensional tensor of voxels that indicates to which segmentation class each voxel belongs.

Similarly, although the herein disclosure mainly describes various embodiments of the subject innovation where the unsupervised modeling 202 is Gaussian mixture modeling that involves identifying constituent two-dimensional Gaussian distributions, this is a mere non-limiting example. Those having ordinary skill in the art will appreciate that multivariate Gaussian mixture modeling can be applied in various embodiments (e.g., instead of identifying means and variances, multivariate Gaussian mixture modeling can involve identifying centroids and covariances).

Likewise, although the herein disclosure mainly describes various embodiments of the subject innovation where the unsupervised modeling 202 is applied to an entire probability distribution of HU values exhibited by the CT image 104, this is a mere non-limiting example. Those having ordinary skill in the art will appreciate that the unsupervised modeling 202 (e.g., Gaussian mixture modeling) can, in various cases, be applied to any suitable number of patches of pixels within the CT image 104, as desired.

Moreover, although the herein disclosure mainly describes various embodiments of the subject innovation that generate image segmentations of the CT image 104, this is a mere non-limiting example. Those having ordinary skill in the art will appreciate that the herein teachings can be readily applied to any suitable type of medical images (e.g., can be applied to improve segmentation of computed tomography images, of magnetic resonance images, of ultrasound images, of positron emission tomography images), even if such medical images utilize pixel values that are not Hounsfield units.

Furthermore, although the herein disclosure mainly describes various embodiments of the subject innovation that apply to the deep-learning model 702, this is a mere non-limiting example. Those having ordinary skill in the art will appreciate that any suitable segmentation model can be enhanced by being configured to receive as input at least one of the set of class probability masks 204 (e.g., the segmentation model can be a neural network, a regression model, a support vector machine).

Various embodiments of the subject innovation relate to the automated segmentation of CT images (e.g., and/or any other suitable medical images). Existing techniques for facilitating automated image segmentation involve single-channel models that are trained in a supervised fashion and that are configured to receive as input only the CT image that is desired to be segmented. As described herein, various embodiments of the subject innovation can provide for significantly improved image segmentation performance via the utilization of unsupervised modeling techniques, such as Gaussian mixture modeling. Specifically, for a CT image that is desired to be segmented, embodiments of the subject innovation can generate, via Gaussian mixture modeling, one or more class probability masks based on the CT image. Then, various embodiments of the subject innovation can feed both the CT image and the one or more class probability masks to a multi-channel segmentation model. As experimentally verified by the inventors, the one or more class probability masks can allow for better initialization and/or regularization of the multi-channel segmentation model, thereby resulting in a better segmentation performance (e.g., better delineation of vessel boundaries, better estimation of cross-sectional area of vessels when three-dimensional CT images are involved), as compared to existing single-channel segmentation models. Moreover, as experimentally verified by the inventors, the one or more class probability masks further allow the multi-channel segmentation model to learn more quickly and/or with significantly less (e.g., 20% less) training data, as compared to existing single-channel segmentation models.

To facilitate some of the above-described machine learning aspects of various embodiments of the subject innovation, consider the following discussion of artificial intelligence. Various embodiments of the present innovation herein can employ artificial intelligence (AI) to facilitate automating one or more features of the present innovation. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) of the present innovation, components of the present innovation can examine the entirety or a subset of the data to which it is granted access and can provide for reasoning about or determine states of the system and/or environment from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes and/or systems (e.g., support vector machines, neural networks, expert systems, Bayesian belief networks, fuzzy logic, data fusion engines, and so on) in connection with performing automatic and/or determined action in connection with the claimed subject matter. Thus, classification schemes and/or systems can be used to automatically learn and perform a number of functions, actions, and/or determinations.

A classifier can map an input attribute vector, z=(z1, z2, z3, z4, zn), to a confidence that the input belongs to a class, as by f(z)=confidence(class). Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence, any of which can be employed. Classification as used herein also is inclusive of statistical regression that is utilized to develop models of priority.

Figure 11:
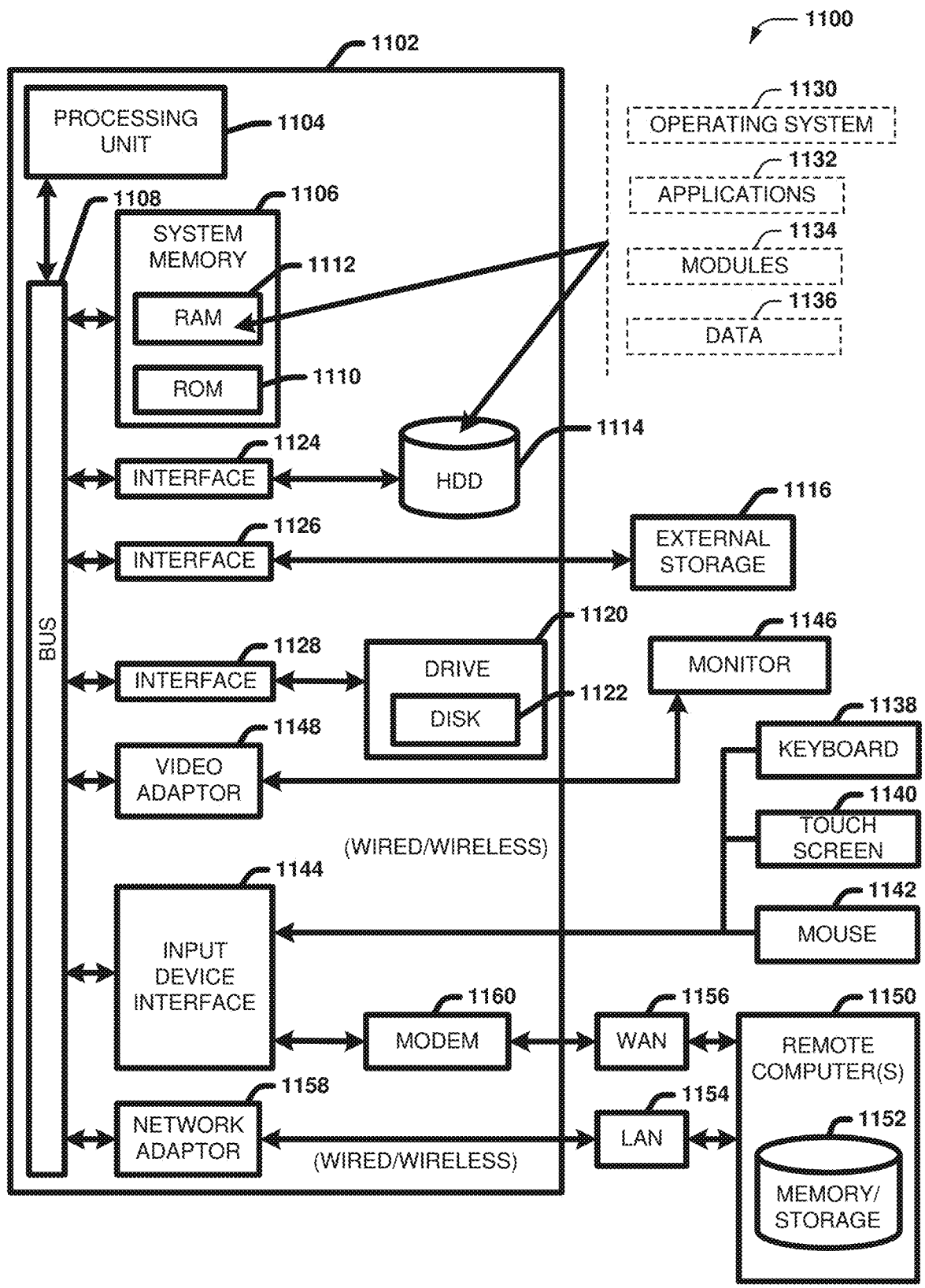
FIG. 11 illustrates a block diagram of an example, non-limiting operating environment in which one or more embodiments described herein can be facilitated.

In order to provide additional context for various embodiments described herein, FIG. 11 and the following discussion are intended to provide a brief, general description of a suitable computing environment 1100 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random-access memory (RAM), read-only memory (ROM), electrically erasable programmable read-only memory (EEPROM), flash memory or other memory technology, compact disk read-only memory (CD ROM), digital versatile disk (DVD), Blu-ray disc (BD) or other optical disk storage, magnetic cassettes, magnetic tape, magnetic disk storage or other magnetic storage devices, solid-state drives or other solid-state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 11, the example environment 1100 for implementing various embodiments of the aspects described herein includes a computer 1102, the computer 1102 including a processing unit 1104, a system memory 1106 and a system bus 1108. The system bus 1108 couples system components including, but not limited to, the system memory 1106 to the processing unit 1104. The processing unit 1104 can be any of various commercially-available processors. Dual microprocessors and other multi-processor architectures can also be employed as the processing unit 1104.

The system bus 1108 can be any of several types of bus structure that can further interconnect to a memory bus (with or without a memory controller), a peripheral bus, and a local bus using any of a variety of commercially-available bus architectures. The system memory 1106 includes ROM 1110 and RAM 1112. A basic input/output system (BIOS) can be stored in a non-volatile memory such as ROM, erasable programmable read-only memory (EPROM), EEPROM, which BIOS contains the basic routines that help to transfer information between elements within the computer 1102, such as during startup. The RAM 1112 can also include a high-speed RAM such as static RAM for caching data.

The computer 1102 further includes an internal hard disk drive (HDD) 1114 (e.g., EIDE, SATA), one or more external storage devices 1116 (e.g., a magnetic floppy disk drive (FDD), a memory stick or flash drive reader, a memory card reader, etc.) and a drive 1120, e.g., such as a solid-state drive, an optical disk drive, which can read or write from a disk 1122, such as a CD-ROM disc, a DVD, a BD, etc. Alternatively, where a solid-state drive is involved, disk 1122 would not be included, unless separate. While the internal HDD 1114 is illustrated as located within the computer 1102, the internal HDD 1114 can also be configured for external use in a suitable chassis (not shown). Additionally, while not shown in environment 1100, a solid-state drive (SSD) could be used in addition to, or in place of, an HDD 1114. The HDD 1114, external storage device(s) 1116 and drive 1120 can be connected to the system bus 1108 by an HDD interface 1124, an external storage interface 1126 and a drive interface 1128, respectively. The interface 1124 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1102, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1112, including an operating system 1130, one or more application programs 1132, other program modules 1134, and program data 1136. All or portions of the operating system, applications, modules, and/or data can also be cached in the RAM 1112. The systems and methods described herein can be implemented utilizing various commercially-available operating systems or combinations of operating systems.

Computer 1102 can optionally comprise emulation technologies. For example, a hypervisor (not shown) or other intermediary can emulate a hardware environment for operating system 1130, and the emulated hardware can optionally be different from the hardware illustrated in FIG. 11. In such an embodiment, operating system 1130 can comprise one virtual machine (VM) of multiple VMs hosted at computer 1102. Furthermore, operating system 1130 can provide runtime environments, such as the Java runtime environment or the .NET framework, for applications 1132. Runtime environments are consistent execution environments that allow applications 1132 to run on any operating system that includes the runtime environment. Similarly, operating system 1130 can support containers, and applications 1132 can be in the form of containers, which are lightweight, standalone, executable packages of software that include, e.g., code, runtime, system tools, system libraries and settings for an application.

Further, computer 1102 can be enabled with a security module, such as a trusted processing module (TPM). For instance with a TPM, boot components hash next-in-time boot components, and wait for a match of results to secured values, before loading a next boot component. This process can take place at any layer in the code execution stack of computer 1102, e.g., applied at the application execution level or at the operating system (OS) kernel level, thereby enabling security at any level of code execution.

A user can enter commands and information into the computer 1102 through one or more wired/wireless input devices, e.g., a keyboard 1138, a touch screen 1140, and a pointing device, such as a mouse 1142. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1104 through an input device interface 1144 that can be coupled to the system bus 1108, but can be connected by other interfaces, such as a parallel port, an IEEE 1394 serial port, a game port, a USB port, an IR interface, a BLUETOOTH® interface, etc.

A monitor 1146 or other type of display device can be also connected to the system bus 1108 via an interface, such as a video adapter 1148. In addition to the monitor 1146, a computer typically includes other peripheral output devices (not shown), such as speakers, printers, etc.

The computer 1102 can operate in a networked environment using logical connections via wired and/or wireless communications to one or more remote computers, such as a remote computer(s) 1150. The remote computer(s) 1150 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1152 is illustrated. The logical connections depicted include wired/wireless connectivity to a local area network (LAN) 1154 and/or larger networks, e.g., a wide area network (WAN) 1156. Such LAN and WAN networking environments are commonplace in offices and companies, and facilitate enterprise-wide computer networks, such as intranets, all of which can connect to a global communications network, e.g., the Internet.

When used in a LAN networking environment, the computer 1102 can be connected to the local network 1154 through a wired and/or wireless communication network interface or adapter 1158. The adapter 1158 can facilitate wired or wireless communication to the LAN 1154, which can also include a wireless access point (AP) disposed thereon for communicating with the adapter 1158 in a wireless mode.

When used in a WAN networking environment, the computer 1102 can include a modem 1160 or can be connected to a communications server on the WAN 1156 via other means for establishing communications over the WAN 1156, such as by way of the Internet. The modem 1160, which can be internal or external and a wired or wireless device, can be connected to the system bus 1108 via the input device interface 1144. In a networked environment, program modules depicted relative to the computer 1102 or portions thereof, can be stored in the remote memory/storage device 1152. It will be appreciated that the network connections shown are example and other means of establishing a communications link between the computers can be used.

When used in either a LAN or WAN networking environment, the computer 1102 can access cloud storage systems or other network-based storage systems in addition to, or in place of, external storage devices 1116 as described above, such as but not limited to a network virtual machine providing one or more aspects of storage or processing of information. Generally, a connection between the computer 1102 and a cloud storage system can be established over a LAN 1154 or WAN 1156 e.g., by the adapter 1158 or modem 1160, respectively. Upon connecting the computer 1102 to an associated cloud storage system, the external storage interface 1126 can, with the aid of the adapter 1158 and/or modem 1160, manage storage provided by the cloud storage system as it would other types of external storage. For instance, the external storage interface 1126 can be configured to provide access to cloud storage sources as if those sources were physically connected to the computer 1102.

The computer 1102 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 12:
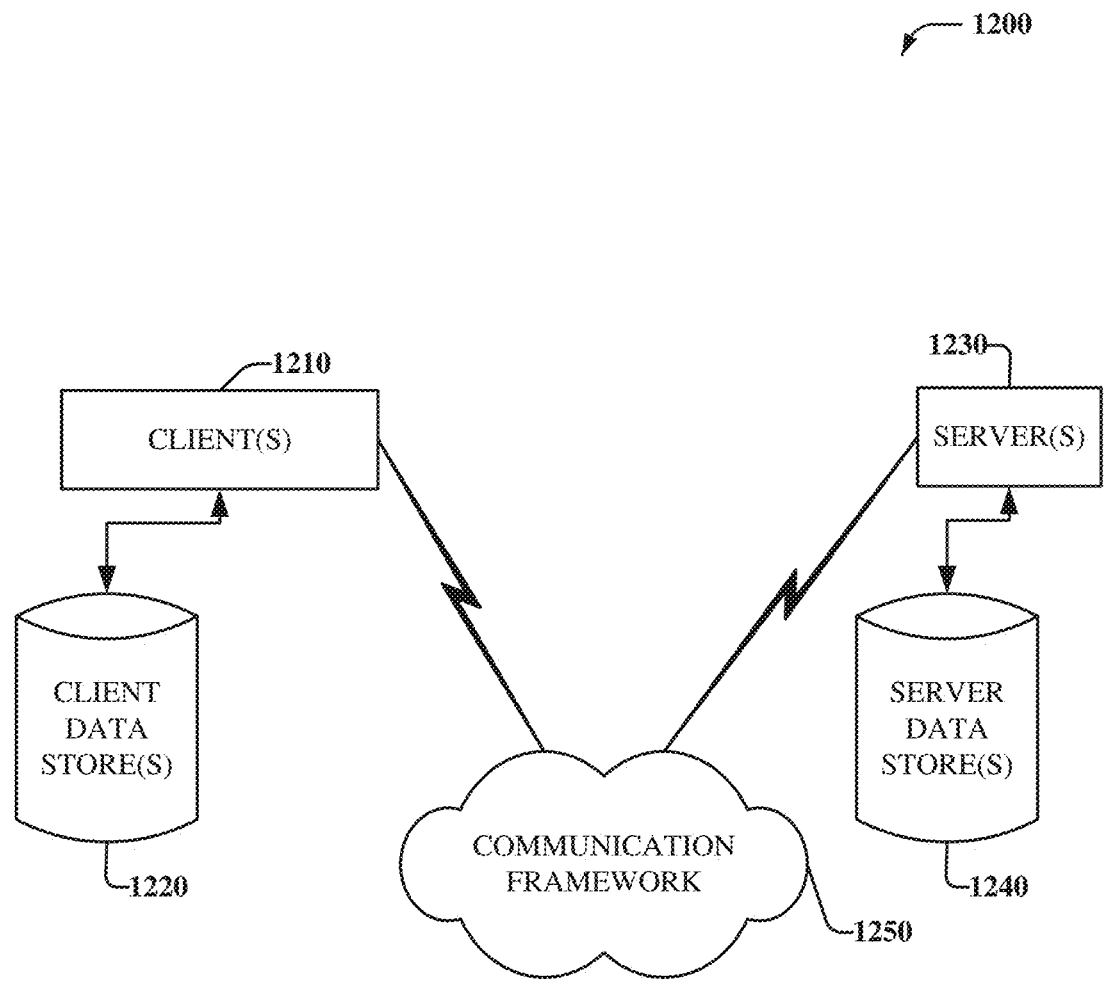
FIG. 12 illustrates an example networking environment operable to execute various implementations described herein.

FIG. 12 is a schematic block diagram of a sample computing environment 1200 with which the disclosed subject matter can interact. The sample computing environment 1200 includes one or more client(s) 1210. The client(s) 1210 can be hardware and/or software (e.g., threads, processes, computing devices). The sample computing environment 1200 also includes one or more server(s) 1230. The server(s) 1230 can also be hardware and/or software (e.g., threads, processes, computing devices). The servers 1230 can house threads to perform transformations by employing one or more embodiments as described herein, for example. One possible communication between a client 1210 and a server 1230 can be in the form of a data packet adapted to be transmitted between two or more computer processes. The sample computing environment 1200 includes a communication framework 1250 that can be employed to facilitate communications between the client(s) 1210 and the server(s) 1230. The client(s) 1210 are operably connected to one or more client data store(s) 1220 that can be employed to store information local to the client(s) 1210. Similarly, the server(s) 1230 are operably connected to one or more server data store(s) 1240 that can be employed to store information local to the servers 1230.

The present invention may be a system, a method, an apparatus and/or a computer program product at any possible technical detail level of integration. The computer program product can include a computer-readable storage medium (or media) having computer-readable program instructions thereon for causing a processor to carry out aspects of the present invention. The computer-readable storage medium can be a tangible device that can retain and store instructions for use by an instruction execution device. The computer-readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium can also include the following: a portable computer diskette, a hard disk, a random-access memory (RAM), a read-only memory (ROM), an erasable programmable read-only memory (EPROM or Flash memory), a static random-access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device. Computer-readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer-readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer-readable program instructions by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer-readable program instructions. These computer-readable program instructions can be provided to a processor of a general purpose computer, special-purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions can also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks. The computer-readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special-purpose hardware-based systems that perform the specified functions or acts or carry out combinations of special-purpose hardware and computer instructions.

While the subject matter has been described above in the general context of computer-executable instructions of a computer program product that runs on a computer and/or computers, those skilled in the art will recognize that this disclosure also can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer-readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read-only memory (ROM), programmable ROM (PROM), electrically programmable ROM (EPROM), electrically erasable PROM (EEPROM), flash memory, or non-volatile random-access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
  a processor that executes computer-executable components stored in a computer-readable memory, the computer-executable components comprising:
    a receiver component that accesses a computed tomography (CT) image depicting an anatomical structure;
    a probability component that generates, via an unsupervised modeling technique, at least one class probability mask of the anatomical structure based on the CT image, wherein each class probability mask of the at least one class probability mask comprises respective probability values for pixels of the CT image indicating respective probabilities of the pixels belonging to an anatomical class associated with a class probability mask of respective anatomical classes associated with the at least one class probability mask; and
    an execution component that generates, via a deep-learning model, an image segmentation of the CT image into the respective anatomical classes based on the CT image and the at least one class probability mask.

2. The system of claim 1, wherein the receiver component accesses a training CT image, wherein the probability component generates, via the unsupervised modeling technique, at least one training class probability mask based on the training CT image, and wherein the computer-executable components further comprise:
  a training component that trains the deep-learning model based on the training CT image and the at least one training class probability mask.

3. The system of claim 1, wherein the unsupervised modeling technique is Gaussian mixture modeling, fuzzy C-means clustering, K-means clustering, a generative adversarial network, or an auto-encoder.

4. The system of claim 1, wherein the deep-learning model exhibits a U-Net architecture that comprises an encoder portion and a decoder portion.

5. The system of claim 1, wherein the anatomical structure is a vascular structure.

6. The system of claim 5, wherein the vascular structure is a lumen, and wherein the comprises at least one of a blood class probability mask, a plaque calcification class probability mask, or a background class probability mask.

7. The system of claim 1, wherein the deep-learning model receives as input the CT image and the at least one class probability mask.

8. A computer-implemented method, comprising:
  accessing, by a device operatively coupled to a processor, a computed tomography (CT) image depicting an anatomical structure;
  generating, by the device and via an unsupervised modeling technique, at least one class probability mask of the anatomical structure based on the CT image, wherein each class probability mask of at least one class probability mask comprises respective probability values for pixels of the CT image indicating respective probabilities of the pixels belonging to an anatomical class associated with the class probability mask of respective anatomical classes associated with the at least one class probability mask; and
  generating, by the device and via a deep-learning model, an image segmentation of the CT image into the respective anatomical classes based on the CT image and the at least one class probability mask.

9. The computer-implemented method of claim 8, further comprising:
  accessing, by the device, a training CT image;
  generating, by the device and via the unsupervised modeling technique, at least one training class probability mask based on the training CT image; and training, by the device, the deep-learning model based on the training CT image and the at least one training class probability mask.

10. The computer-implemented method of claim 8, wherein the unsupervised modeling technique is Gaussian mixture modeling, fuzzy C-means clustering, K-means clustering, a generative adversarial network, or an auto-encoder.

11. The computer-implemented method of claim 8, wherein the deep-learning model exhibits a U-Net architecture that comprises an encoder portion and a decoder portion.

12. The computer-implemented method of claim 8, wherein the anatomical structure is a vascular structure.

13. The computer-implemented method of claim 12, wherein the vascular structure is a lumen, and wherein the comprises at least one of a blood class probability mask, a plaque calcification class probability mask, or a background class probability mask.

14. The computer-implemented method of claim 8, wherein the deep-learning model receives as input the CT image and the at least one class probability mask.

15. A computer program product for facilitating hybrid unsupervised and supervised image segmentation, the computer program product comprising a computer-readable memory having program instructions embodied therewith, the program instructions executable by a processor to cause the processor to:
  access a computed tomography (CT) image depicting an anatomical structure;
  generate, via an unsupervised modeling technique, at least one class probability mask of the anatomical structure based on the CT image, wherein each class probability mask of the at least one class probability mask comprises respective probability values for pixels of the CT image indicating respective probabilities of the pixels belonging to an anatomical class associated with the class probability mask of respective anatomical classes associated with the at least one class probability mask; and
  generate, via a deep-learning model, an image segmentation of the CT image into the respective anatomical classes based on the CT image and the at least one class probability mask.

16. The computer program product of claim 15, wherein the program instructions are further executable to cause the processor to:
  access a training CT image;
  generate, via the unsupervised modeling technique, at least one training class probability mask based on the training CT image; and
  train the deep-learning model based on the training CT image and the at least one training class probability mask.

17. The computer program product of claim 15, wherein the unsupervised modeling technique is Gaussian mixture modeling, fuzzy C-means clustering, K-means clustering, a generative adversarial network, or an auto-encoder.

18. The computer program product of claim 15, wherein the deep-learning model exhibits a U-Net architecture that comprises an encoder portion and a decoder portion.

19. The computer program product of claim 15, wherein the anatomical structure is a vascular structure.

20. The computer program product of claim 19, wherein the vascular structure is a lumen, and wherein the comprises at least one of a blood class probability mask, a plaque calcification class probability mask, or a background class probability mask.

\* \* \* \* \*